United States Patent
Haschemi et al.

(10) Patent No.: US 9,694,026 B2
(45) Date of Patent: Jul. 4, 2017

(54) USE OF SEDOHEPTULOSE FOR PREVENTION OR TREATMENT OF INFLAMMATION

(71) Applicant: C7 SUGAR GMBH, Vienna (AT)

(72) Inventors: Arvand Haschemi, Vienna (AT); Oswald Wagner, Vienna (AT); Csörsz Nagy, Vienna (AT); Rodrig Marculescu, Altenberg (AT)

(73) Assignee: C7 SUGAR GMBH, Vienna (AT)

( * ) Notice: Subject to any disclaimer, the term of this patent is extended or adjusted under 35 U.S.C. 154(b) by 0 days.

(21) Appl. No.: 14/778,850

(22) PCT Filed: Mar. 21, 2014

(86) PCT No.: PCT/EP2014/055679
§ 371 (c)(1),
(2) Date: Sep. 21, 2015

(87) PCT Pub. No.: WO2014/147214
PCT Pub. Date: Sep. 25, 2014

(65) Prior Publication Data
US 2016/0045525 A1    Feb. 18, 2016

(30) Foreign Application Priority Data

Mar. 21, 2013    (EP) .................................... 13160443

(51) Int. Cl.
*A61K 31/7004*    (2006.01)
*A01N 1/02*    (2006.01)
*A61K 45/06*    (2006.01)

(52) U.S. Cl.
CPC ........ *A61K 31/7004* (2013.01); *A01N 1/0226* (2013.01); *A61K 45/06* (2013.01)

(58) Field of Classification Search
None
See application file for complete search history.

(56) References Cited

U.S. PATENT DOCUMENTS

2007/0098818 A1   5/2007   Smith
2009/0252834 A1   10/2009  Hayek et al.

FOREIGN PATENT DOCUMENTS

| EP | 0221728 | 5/1987 |
| JP | 2007137797 | 6/2007 |
| WO | WO2009/066822 | 5/2009 |

OTHER PUBLICATIONS

Zuo, CN 101919872, Dec. 22, 2010, machine translation.*
Adams, The Journal of Nutrition, Jul. 2006;136(7): 1886-9.*
Kardon, FEBS Letters 582 (2008) 3330-3334.*
Hernandez-Hernandez, O. et al.: "Determination of Free Inositols and Other Low Molecular Weight Carbohydrates in Vegetables", Journal of Agricultural and Food Chemistry, vol. 59, (2011), pp. 2451-2455.
Herrman, J.L. et al.: "Hepatic Carbamyl Phosphate: Glucose Phosphotransferase—Sistribution, Comparative Kinetics, and Responses to Alloxan- or Mannoheptulose-Induced Diabetes", Archives Of Biochemistry And Biophysics, vol. 152, (1972), pp. 180-186.
Soria, A.C. et al.: "Determination of minor carbohydrates in carrot (*Daucus carota* L.) by GC-MS", Food Chemistry, vol. 114, (2009), pp. 758-762.
Haschemi, A. et al.: "The Sedoheptulose Kinase CARKL Directs Macrophage Polarization through Control of Glucose Metabolism", Cell Metabolism, vol. 15, (Jun. 6, 2015), pp. 813-826.
Jiang, P. et al.: "p53 regulates biosynthesis through direct inactivation of glucose-6-phosphate dehydrogenase", Nat. Cell Biol., vol. 13, No. 3, (2011), pp. 310-316.
Kardon, T. et al.: "Characterization of mammalian sedoheptulokinase and mechanism of formation of erythritol in sedoheptulokinase deficiency", FEBS Letters, vol. 582, (2008), pp. 3330-3334.
Lindroos, J. et al.: "Human but Not Mouse Adipogenesis Is Critically Dependent on LMO3", Cell Metabolism, vol. 18, (Jul. 2, 2013), pp. 62-74.
Nagy, C. et al.: "Sedoheptulose kinase regulates cellular carbohydrate metabolism by sedoheptulose 7-phosphate supply", Biochemical Society Transactions, vol. 41, (2013), pp. 674-680.
Patel, C.J. et al.: "Systematic identification of interaction effects between genome- and environment-wide associations in type 2 diabetes mellitus", Hum Genet, vol. 132, (2013), pp. 495-508.
Ruiz-Matute, A.I. et al.: "Derivatization of carbohydrates for GC and GC-MS analyses", Journal of Chromatography B, 879, (2011), pp. 1226-1240.
Schillinger, M. et al.: "Inflammation and Carotid Artery—Risk for Atherosclerosis Study (ICARAS)", Circulation, vol. 111, (2005), pp. 2203-2209.

* cited by examiner

*Primary Examiner* — Layla Berry
(74) *Attorney, Agent, or Firm* — Norton Rose Fulbright US LLP

(57) ABSTRACT

The invention discloses sedoheptulose for use in the prevention or treatment of inflammation.

11 Claims, 11 Drawing Sheets

USE OF SEDOHEPTULOSE FOR PREVENTION OR TREATMENT OF INFLAMMATION

CROSS-REFERENCE TO RELATED APPLICATIONS

Figure 1:
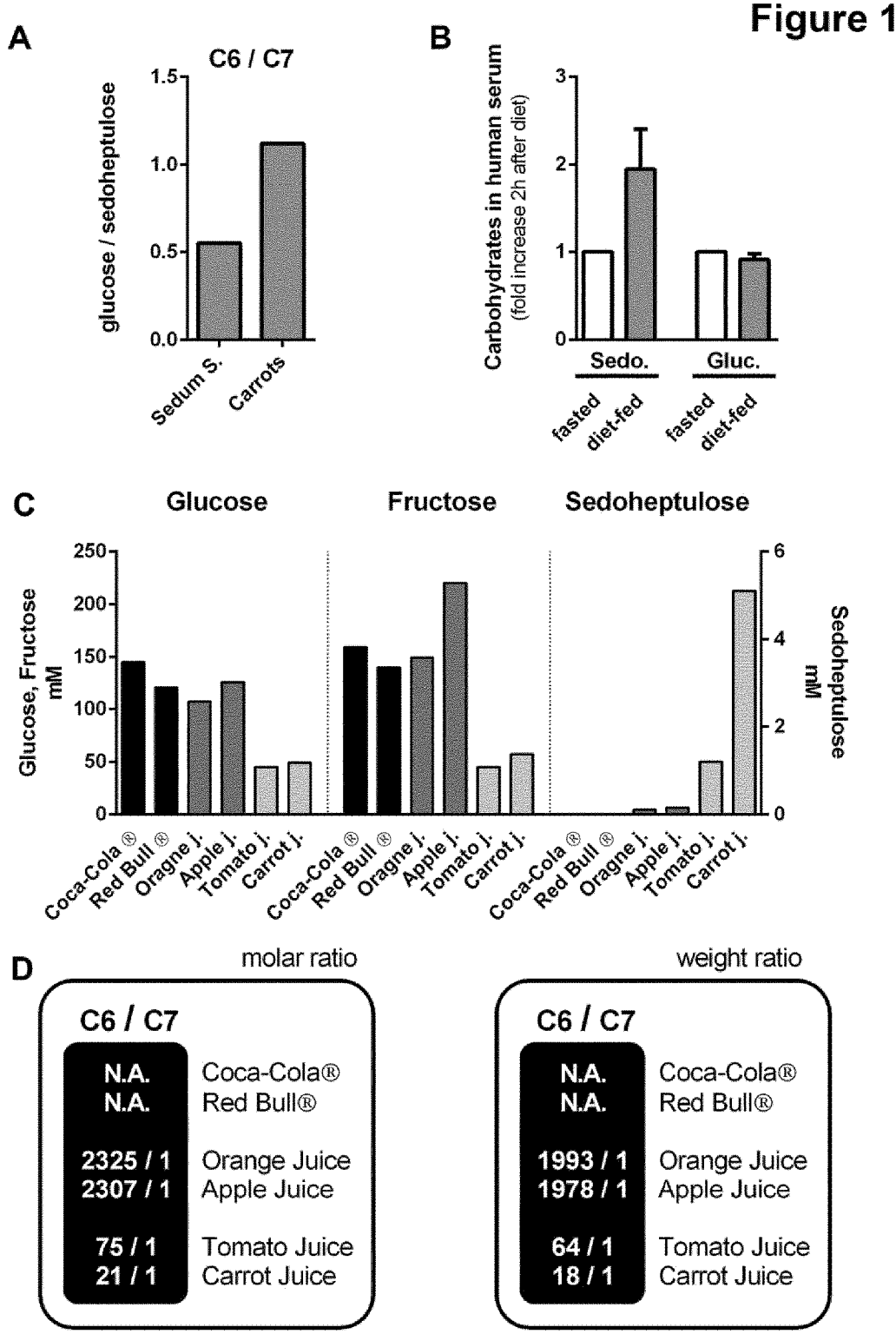

This application is a national phase application under 35 U.S.C. §371 of International Application No. PCT/EP2014/055679 filed 21 Mar. 2014, which claims priority to European Patent Application No. 13160443.1 filed 21 Mar. 2013. The entire contents of each of the above-referenced disclosures is specifically incorporated by reference herein without disclaimer.

The technical field of the present invention is the prevention or treatment of inflammation.

Inflammation is part of the complex biological response of vascular tissues to harmful stimuli, such as pathogens, damaged cells, or irritants. The classical signs of acute inflammation are pain, heat, redness, swelling and loss of function. Inflammation is a protective attempt by the organism to remove the injurious stimuli and to initiate the healing process. Inflammation is a stereotyped response, and therefore it is considered as a mechanism of innate immunity, as compared to adaptive immunity, which is specific for each pathogen.

Inflammation can be classified as either acute or chronic. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system and various cells within the injured tissue. Prolonged inflammation, known as chronic inflammation, leads to a progressive shift in the type of cells present at the site of inflammation and is characterized by simultaneous destruction and healing of the tissue from the inflammatory process.

Inflammatory abnormalities (inflammatory disorders) are a large group of disorders which underlie a vast variety of human diseases. The immune system is often involved with inflammatory disorders, demonstrated in both allergic reactions and some myopathies, with many immune system disorders resulting in abnormal inflammation. Non-immune diseases with etiological origins in inflammatory processes include cancer, atherosclerosis and ischaemic heart disease. Examples of disorders associated with inflammation include acne vulgaris, asthma, autoimmune diseases, celiac disease, chronic prostatitis, glomerulonephritis, hypersensitivities, inflammatory bowel diseases, pelvic inflammatory disease, reperfusion injury, rheumatoid arthritis, sarcoidosis, transplant rejection, vasculitis, interstitial cystitis, atherosclerosis, allergy, myopathies, leucocyte defects and cancer.

Medical treatment of acute and chronic inflammation has been performed with corticosteroids or non-steroidal anti-inflammatory drugs (NSAIDs).

Also anti-inflammatory foods have been suggested to treat or prevent inflammation. Prostaglandins are hormone-like substances that affect the body in variety of ways, also regulating inflammatory mediation. An anti-inflammatory diet includes less food that create inflammation-causing prostaglandins (PGE2) in the body, and more foods that create anti-inflammatory prostaglandins (PGE1 and PGE3). Suggested diets to prevent inflammation include those rich in vegetables and low in simple carbohydrates and fats, such as saturated fats and trans-fats. Anti-inflammatory foods include most colourful fruits and vegetables, oily fish (which contain higher levels of omega-3 fatty acids), nuts, seeds and certain spices, such as ginger. Extra-virgin olive oil contains the chemical oleocanthal that acts similarly to ibuprofen. Omega-3 fatty acids have been shown to disrupt inflammation cell signaling pathways by binding to the GPR120 receptor.

However, there is still a need for prevention and treatment of inflammation, especially chronic inflammation. Such prevention and treatment should be provided without severe side effects or, preferably, without the risk for long term adverse developments, such as addiction, metabolic disorders, declining efficacy, etc.

Therefore, the present invention provides sedoheptulose for use in the prevention or treatment of inflammation.

Sedoheptulose (CAS number: 3019-74-7; PubChem: 5459879; ChemSpider: 4573620; MeSH: sedoheptulose; ChEBI: CHEBI:16802) or D-altro-heptulose is a ketoheptose—a monosaccharide with seven carbon atoms and a ketone functional group. It is one of the few heptoses found in nature. Sedoheptulose is producible by extraction from natural sources or by chemical synthesis. It can be purified to high purity degrees (e.g. >60% purity, preferably >85% purity, more preferred >90% purity, more preferred >95% purity, even more preferred >99% purity, especially >99.9% purity).

Sedoheptulose is a relatively unknown metabolite compared to its phosphorylated form, sedoheptulose-7-phosphate (S7P), which is recognised as an intermediate molecule of primary glucose metabolism. The natural existence of sedoheptulose, a ketoheptose, was first reported in plants and was subsequently identified in human urine, blood spots and recently, within mouse cells. S7P is derived from the transketolase-catalysed conversion of ribose-5-phosphate (R5P) and xylulose-5-phosphate (X5P). This reaction occurs in the non-oxidative arm of the pentose phosphate pathway and generates glyceraldehyde-3-phosphate (G3P), a key glycolytic intermediate, in addition to S7P. G3P and S7P are also produced by transaldolase using fructose-6-phosphate (F6P) and erythrose-4-phosphate (E4P) as substrates. S7P is thus a crucial intermediate in the non-oxidative PPP and S7P bioavailability therefore contributes to cellular carbon flux. Recently, data from several groups have indicated that sedoheptulose kinase may also produce S7P by direct phosphorylation of sedoheptulose (Haschemi et al., Cell Metab. 15 (2012), 813-826). This finding demonstrated the unexpected existence of an additional carbon source, sedoheptulose, which actively participates in cellular carbon metabolism.

Free sedoheptulose can either be diet-derived from fruits and vegetables or formed enzymatically by the dephosphorylation of endogenously produced S7P. Thus far, no specific sedoheptulose transporter or S7P-specific phosphatase has been reported. Other bio-active heptoses include the phenolic compound 7-O-Galloyl-sedoheptulose (GS), mannoheptulose and glucoheptose. GS was reported to be protective in diabetic injury of the kidney by alleviating inflammatory responses. Mannoheptulose (various patents pending) is an isomer of sedoheptulose and a potent hexokinase inhibitor commonly found in avocados. Glycoheptose, although the chemical nature of this compound remains unidentified, has been shown to serve as accessible carbohydrate source in rabbits. Sedoheptulosan is the anhydride of sedoheptulose and might also serve as source for free sedoheptulose.

Free sedoheptulose can be isolated, e.g. from the plant sedum spectabile and has been previously reported to contain high amounts of heptose-carbohydrates.

Sedoheptulose kinase phosphorylates free sedoheptulose, which enables cells to directly route sedoheptulose to carbohydrate metabolism, similar to hexokinase and glucose. According to the present invention, sedoheptulose is a direct carbon source that feeds primary carbohydrate catabolism and anabolism, whereupon CARKL constitutes its entry point. Sedoheptulose can therefore surprisingly be compared to glucose and fructose because these compounds all exist as free carbohydrates and phosphorylated forms. To enter metabolism, free carbohydrates are energetically activated by an initial phosphorylation event. Hexokinase phosphorylates glucose to form G6P and is a key determinant of cellular glucose flux. Fructose is phosphorylated by ketohexokinase to form fructose-1-phosphate (F1P), which must first be converted by aldolase to glyceraldehyde and dihydroxyacetone phosphate (DHAP). DHAP can then directly enter the carbon-cycle, whereas glyceraldehyde must be further phosphorylated. The formation of S7P from sedoheptulose by sedoheptulose kinase, in a manner analogous to G6P formation from glucose by hexokinase, enables free sedoheptulose to readily enter the catabolic system. It was also reported that F6P phosphorylation is competitively inhibited in the presence of high S7P concentrations. Interestingly, fractions containing fructose 1,6-bisphosphatase (FBPase) were also reported to possess sedoheptulose 1,7-bisphosphatase (SBPase) activity.

The present invention therefore is also based on a co-existence of the hexose- and heptose-(bis)phosphate shunts. Notably, high glucose levels or incubation with F2,6bP augmented the S1,7bP formation in perfused rat liver and in rat liver cytosol, respectively. Glucagon, in contrast to high glucose, favoured S1,7bP dephosphorylation and therefore S7P formation. These results show that sedoheptulose metabolism is sensitive to hormonal control.

Sedoheptulose metabolism participates in metabolic regulation; in fact, sedoheptulose directs metabolic fluxes by providing an S7P supply independently from glucose. Increased CARKL expression (and therefore increased sedoheptulose consumption) in a mouse macrophage cell line resulted in reduced G3P, X5P and R5P steady state levels, whereas CARKL knockdown showed the reverse effect. Notably, the basal sedoheptulose levels were not changed by CARKL perturbation. The S7P levels were not changed by overexpression but decreased significantly by CARKL loss, indicating sedoheptulose phosphorylation as a rate-limiting factor for glycolysis-derived G3P distribution. Therefore, the regulation of S7P availability might be the mechanism by which CARKL or excessive amounts of sedoheptulose modulate cellular metabolism.

The present invention is therefore directed to use of C7, e.g. to balance C6-(over)consumption, obesity, diabetes, immune function and—generally—vertebrate's energy utilization. The C7 supplement therefore also provides an effective strategy to manage physiological redox-regulation and thereby also related disorders. With the present invention, it turned out that, both, high sedoheptulose and high sedoheptulose kinase results in enhanced sedoheptulose turn-over. Moreover, tissue expression of sedoheptulose kinase reveals that metabolic organs such as liver or adipose-tissue have the capability to consume sedoheptulose. Additionally, brown-adipose tissue (burns high amounts of lipids) express significantly more (~2.5×) sedoheptulose kinase than white-adipose tissue.

Sedoheptulose (and/or other heptoses), administered to patients having inflammation or being at risk of suffering from inflammation, minimizes the glycemic-load and positively contributes to prevent e.g. diet-induced obesity and/or diabetes. Furthermore, data from transgenic sedoheptulose kinase animals—as model for enhanced sedoheptulose metabolism—show that high sedoheptulose metabolism increases lipid-oxidation (indicated by lower RQ values). This is a beneficial effect of enhanced sedoheptulose turnover. Also energy expenditure is lower in animals with high sedoheptulose turnover. Furthermore, it appears that CARKL mice are more insulin sensitive than control animals. Taken together, this again shows that sedoheptulose metabolism is an effective mean to regulate the metabolic-phenotype in vertebrates.

With the present invention, specific and surprising anti-inflammatory effects could be shown to be caused by high sedoheptulose turnover: Enhanced inflammation plays an important role in the development of diseases, such as obesity related disorders like insulin resistance. In a functional kinase screen for novel regulators of macrophages activation, sedoheptulose kinase was found to repress the lipopolysaccharide (LPS) induced tumour necrosis factor α secretion. In the same screen, overexpression of hexokinase, ketohexokinase and phosphofructokinase (high glucose/fructose metabolism) had the opposite effect. This showed opposite effects of hexose and heptose-carbohydrate metabolism: heptose inhibit inflammation. Moreover, increased CARKL expression repressed LPS-induced macrophage activation and resulted in blunted intracellular superoxide formation, whereas loss of CARKL (mimics reduced sedoheptulose metabolism) enhanced the inflammatory response of those cells.

In addition to these effects, it was shown in the course of establishing the present invention that cytokine production is decreased after inflammation (elicited by LPS injections) in CARKL overexpressing animals compared to wild-type controls as well as in adipose tissue of CARKL mice, or by sedoheptulose supplementation of the latter tissue ex-vivo Together, this showed that administration of sedoheptulose dampens inflammation and therefore positively affects healthcare-related aspects of patients having or being at risk for inflammatory diseases, especially chronic inflammatory diseases. Chronic inflammatory diseases according to the present invention are defined as persistent inflammation, local or systemic, of any etiology, known (like for instance persistent infection) or currently unknown (like for instance sarcoidosis or most cases of chronic rhinosinusitis).

Preferred inflammations to be prevented or treated according to the present invention are systemic inflammatory response syndrome (SIRS), sepsis, meta-inflammation, inflammaging, inflammation in the pathogenesis of an inflammation-related disorder, inflammation in the pathogenesis and inflammation in the course of acute or chronic transplant rejection. Accordingly, a preferred inflammation according to the present invention is wherein the inflammation is SIRS or sepsis, defined as massive systemic inflammation, especially in response to polytrauma or infection, including all the organ-specific manifestations, especially acute respiratory distress syndrome (ARDS) or multiple organ dysfunction syndrome (MODS).

Another preferred inflammation according to the present invention is wherein the inflammation is meta-inflammation or inflammaging, defined as chronic (low grade) systemic inflammation as reflected by increased levels of pro-inflammatory cytokines (like for instance tumor necrosis factor alpha or interleukin-6) or other inflammation markers (like for instance c-reactive protein or serum amyloid alpha) in peripheral blood and involved in aging, adiposity, atherosclerosis, impaired glucose tolerance and type 2 diabetes, neurodegenerative disorders, like dementia, major depressive disorder (MDD) and cancer.

Another preferred inflammation according to the present invention is wherein the inflammation is involved, causally or otherwise, in the pathogenesis of an inflammation-related disorder, especially adiposity, impaired glucose tolerance, diabetes mellitus and diabetic complications, metabolic syndrome, atherosclerosis, inflammatory bowel disease (Crohn's disease, colitis ulcerosa and rarer entities), chronic inflammatory liver disease including chronic viral hepatitis, autoimmune hepatitis, primary sclerosing cholangitis and fatty liver disease in all stages, chronic obstructive pulmonary disease (COPD) and asthma bronciale, inflammatory diseases of the central nervous system including multiple sclerosis, Alzheimer's and Parkinson's disease or peripheral nervous system including diabetic polyneuropathy, Guillain-Barre and related syndromes and neuritides/neuropathies associated with autoimmune collagen tissue diseases or chronic infection like for instance Lyme disease, osteoporosis, osteoarthritis, arthritides like rheumatoid arthritis or ankylosing spondylitis and other rheumatic disorders including the entire spectrum of autoimmune connective tissue disorders and myositis, vasculitis of any etiology and manifestation, age-related macular degeneration (AMD) chronic inflammatory skin disorders like psoriasis and atopic dermatitis, periodontitis, major depressive disorder and cancer.

Another preferred inflammation according to the present invention is wherein the inflammation is involved in the pathogenesis of cancer including cancer causation, progression, metastasis, resistance to therapy, relapse after therapy and cancer manifestations, especially cancer-related cachexia, anemia, fatigue and depression. Given the universal involvement of inflammation in the pathogenesis of cancer the present invention is applicable to all cancer entities regardless of tissue origin, differentiation or localization including all types of carcinoma and sarcoma, melanoma and other tumors of neural crest-derived cells, tumors of the central nervous system, leukemia and lymphoma.

Another preferred inflammation according to the present invention is wherein the inflammation is involved in acute or chronic transplant rejection, especially rejection of allogeneic lung, liver, kidney, heart, intestine or pancreatic islet cell transplants or, conversely, in acute or chronic graft-versus-host disease following autologous, syngeneic or allogeneic bone marrow, peripheral blood stem cell (PBSC) or cord blood transplantation.

Other preferred inflammations according to the present invention is selected from the group consisting of an inflammation of adipose tissue, an inflammation of the nervous system (neuroinflammation), an inflammation of blood vessels (vascular inflammation) and an inflammation of the peritoneum especially as a consequence of peritoneal dialysis as used for kidney replacement therapy.

On the other hand, the present invention also relates to the prevention and treatment of all kind of sedoheptulose deficits, i.e. to treat a sedoheptulose deficit so that disorders that are due to such sedoheptulose deficits can be prevented. In order to treat such sedoheptulose deficits, a sedoheptulose containing composition can be administered to a patient having or being at risk of developing such sedoheptulose deficit (or sedoheptulose deficit syndrome), e.g. as nutritional supplement or in combination with food and/or beverages.

Sedoheptulose is not toxic; it is a natural source of carbohydrates for human metabolism. It may therefore be administered in virtually all medically reasonable ways without risking unexpected side effects or adverse reactions.

According to preferred administration dosages, especially single dosage forms, of the present invention, sedoheptulose is administered in an amount of 0.001 to 300 g per daily dosage, preferably in an amount of 0.5 to 200 g per daily dosage, especially in an amount of 1 to 100 g per daily dosage.

Preferred administration of sedoheptulose is performed parentally, subcutaneously, by intravenous, intratumoural subcutaneous, intramuscular or intraperitoneal injection, especially wherein sedoheptulose is administered orally.

Sedoheptulose may virtually be included in almost any pharmaceutical formulation form, including pharmaceutically acceptable excipients. Preferably, sedoheptulose is administered as a powder, granulate, tablet, pellet, capsule or syrup containing sedoheptulose.

According to a preferred embodiment, sedoheptulose is administered in an amount of 0.001 to 300 g, preferably in an amount of 0.5 to 200 g, especially in an amount of 1 to 100 g. These administration dosages are e.g. for a normal 70 to 80 kg human individual but can be adapted easily based on sex, inflammation degree (or risk), other therapeutic regimen, physiological status/fitness of the patient, etc.

According to a preferred embodiment, sedoheptulose is administered in combination with hexokinase inhibitors, preferably mannoheptulose or 2-deoxy-D-glucose. Hexokinase inhibitors are well known in the art and can be applied in the present invention in the amounts and dosages already known or suggested in the prior art to the patient. For example, the inhibitor can be added in an amount of 0.0001% to 50% w/w, especially 0.001% to 1%, relative to the sedoheptulose content (e.g. 0.0001 to 50 mg, if 100 mg sedoheptulose is administered).

According to another embodiment, the present invention relates to a method for storage of human organs for transplantation purposes wherein the organ to be transplanted to a patient is stored in a storage solution comprising sedoheptulose. This aspect is based on the anti-inflammatory capacity of sedoheptulose and serves the same aim of reducing inflammation in the transplant patient (to whom sedoheptulose may be applied as well): The anti-inflammatory property of the sedoheptulose storage solution that is used for impregnating the organ to be transplanted also safeguards the reduction or prevention of inflammatory processes in the isolated organ itself during storage and also after transplantation so that not only anti-inflammatory protection is present in the patient, but also in the organ that has been transplanted.

In a preferred embodiment of this method, the storage solution comprises sedoheptulose in a concentration of 0.001 to 500 mg/ml, preferably in a concentration of 0.01 to 300 mg/ml, especially in a concentration of 0.1 to 150 mg/ml, defined as the concentration of all liquid material attached to or covering the organ to be transplanted (i.e. the solution that remains in the organ storage containment after removing the organ from the containment).

According to another aspect, the present invention also relates to a peritoneal dialysis solution containing sedoheptulose in a concentration of 0.001 to 500 mg/ml, preferably in a concentration of 0.01 to 300 mg/ml, especially in a concentration of 0.1 to 150 mg/ml.

The present invention is further described in the following examples and the figures, yet without being restricted thereto.

FIG. 1: (A) Pooled samples from carrots or leaves of indoor grown Sedum Spectabile plants were analyzed by gas-chromatography coupled to mass spectrometry to specifically measure relative glucose (C6) and sedoheptulose (C7) levels. The ratio of C6/C7 was calculated by dividing their respective peak area. (B) Sedoheptulose and glucose levels were further assessed by GC-MS in serum of individuals before and after food uptake to investigate if diet-derived C7 can enter the human blood-stream. Sedoheptulose and glucose level of four overnight fasted (fasted) individuals (empty bars) were compared to levels measured two hours after a meal (diet-fed, grey bars) containing mainly carrots (~700 g) with some olive-oil, salt and pepper. The change in serum carbohydrate levels was expressed as mean fold change (n=4, +/−S.D.). (C) Concentrations of glucose, fructose and sedoheptulose were measured in the carbohydrate-extracts of indicated beverages. Mean values of four pooled technical replicates were blotted to demonstrate extracted sugar concentrations. Furthermore (D), the C6/C7 (sedoheptulose) ratio was established by dividing the sum of glucose and fructose (C6) molecules or weight by respective sedoheptulose (C7) unit (N.A.=not applicable).

Figure 2:
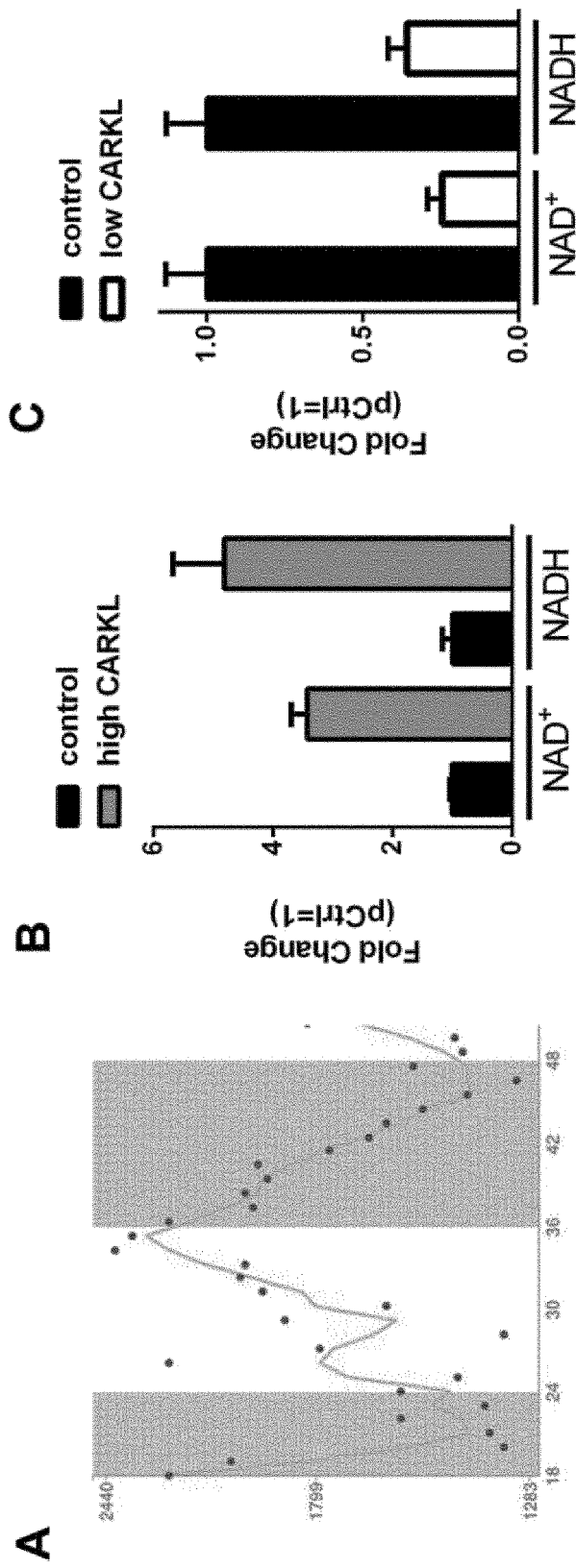
Figure 2:
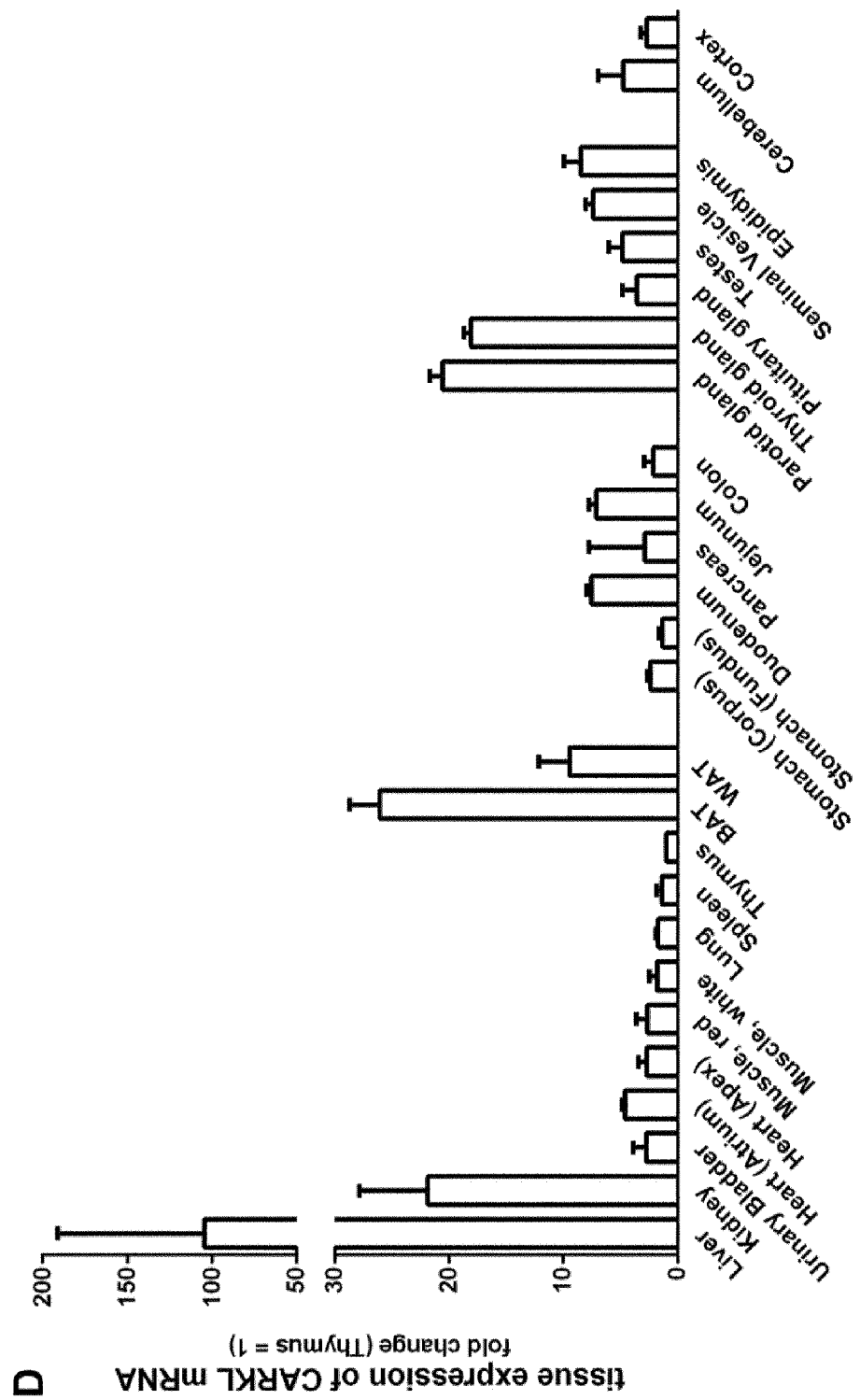

FIG. 2: (A) Blot of normalized sedoheptulose kinase (CARKL) mRNA expression levels in mouse liver over a period of 48 hrs was obtained from the public available "Circadian Gene Expression Database—CIRCA". Y-axis represents normalized gene expression and X-axis time in hours. (B and C) Reduced and oxidized nicotinamide adenine dinucleotide levels of cells with perturbed CARKL expression were calculated from previously recorded metabolomics data (Haschemi et al., 15 (2012), 813-826). RAW264.7 cell line either (B) expressing high CARKL levels by overexpression or (C) low CARKL levels by shRNAmir expression were compared to individual control cell lines to illustrate CARKL mediated nicotinamide adenine dinucleotide regulation. Data represent mean fold change of three individual experiments +/−SEM. (D) CARKL mRNA levels were measured in a mouse cDNA tissue library. Data represents normalized (to β-actin) mean CARKL expression relative to thymus CARKL expression in fold change (all tissues n=3, S.D.).

Figure 3:
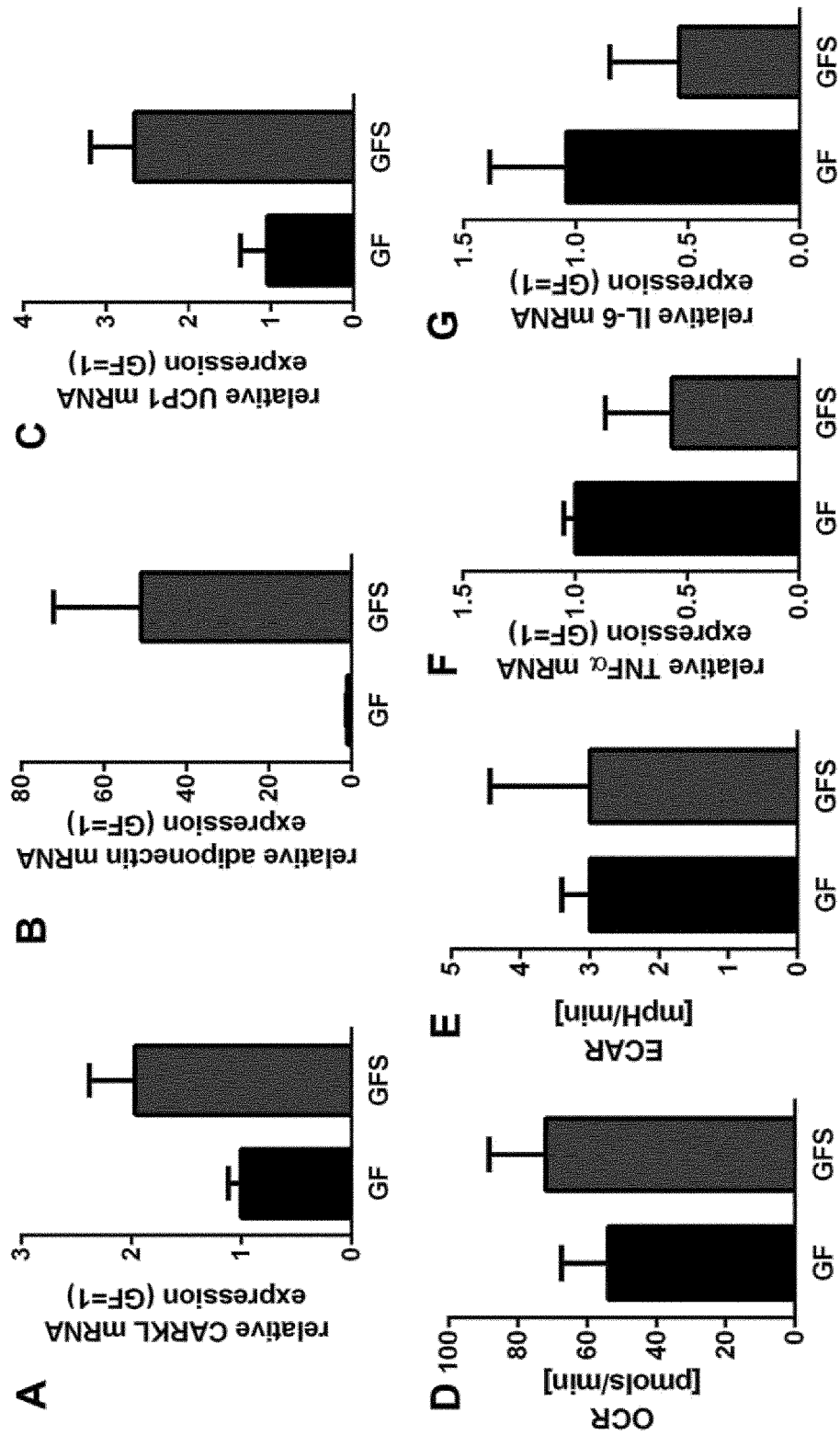
Figure 3:
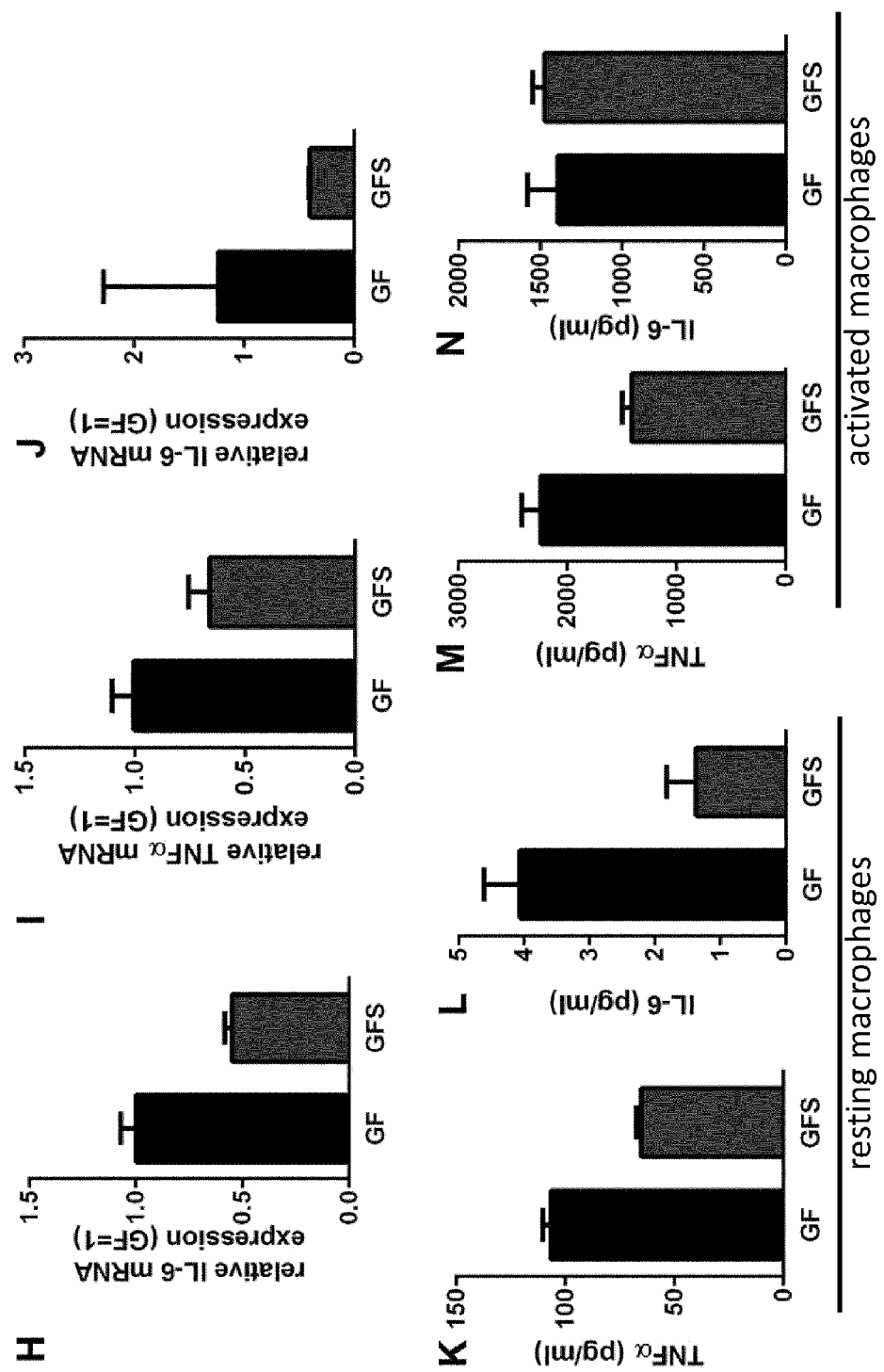

FIG. 3: (A-E) Primary human adipocytes were obtained by differentiation of the stromal vascular cell fraction in the presence of glucose and fructose (GF, 1.5 g/L of each sugar; total carbohydrates 3 g/L) or sedoheptulose supplemented media, which was termed GFS (1 g/L of each sugar; total carbohydrates 3 g/L), for eight days. Subsequently mRNA levels of (A) CARKL, (B) adiponectin and (C) uncoupling protein 1 (UCP-1) was assessed by RT-PCR and compared between the groups. (D) Cellular oxygen consumption rates (OCR) and (E) extracellular acidification rates (ECAR) of adipocytes were recorded in the presence of indicated carbohydrate-mix (mean+/−S.D., n=9-11). (F) Tumor necrosis factor alpha (TNFa) and (G) interleukin 6 (IL-6) mRNA expression levels of mature murine adipocytes cultivated for three days in cell culture media containing either GF or GFS carbohydrate mix, or (H) IL-6 expression in primary murine hepatocytes, as well as (I) TNFa and (J) IL-6 mRNA levels in primary bone marrow derived macrophages, both cell types were pre-cultured for two days in GF or GFS media, were compared between respective groups. Secretion of (K) TNFa and (L) IL-6 cytokines over the period of two days was measured by ELISA in the supernatant of bone marrow derived macrophages. LPS-induced (100 ng/ml) secretion of (M) TNFa 2 hrs after activation and (N) IL-6 6 hrs after activation in the respective media by macrophages was also measured by ELISA. Data represents mean+/−S.D., n=3)

Figure 4:
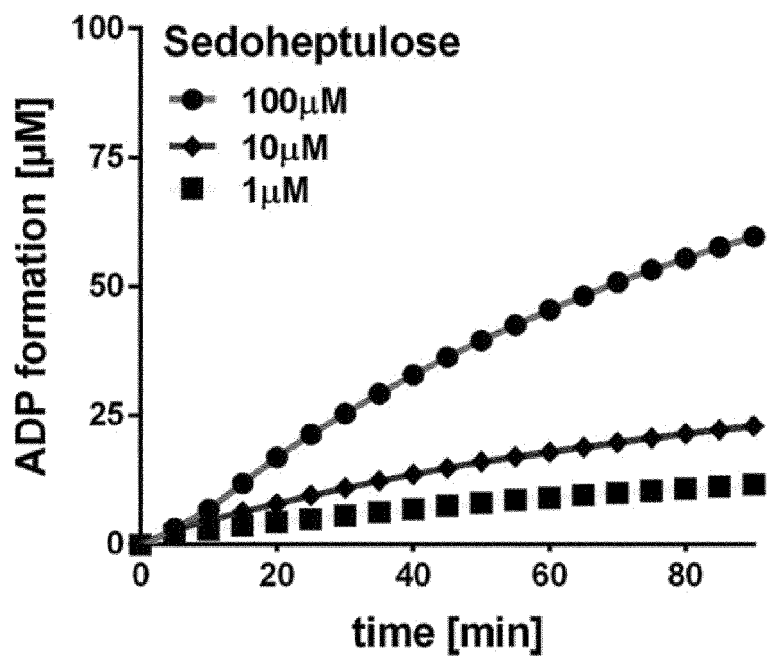
Figure 4:
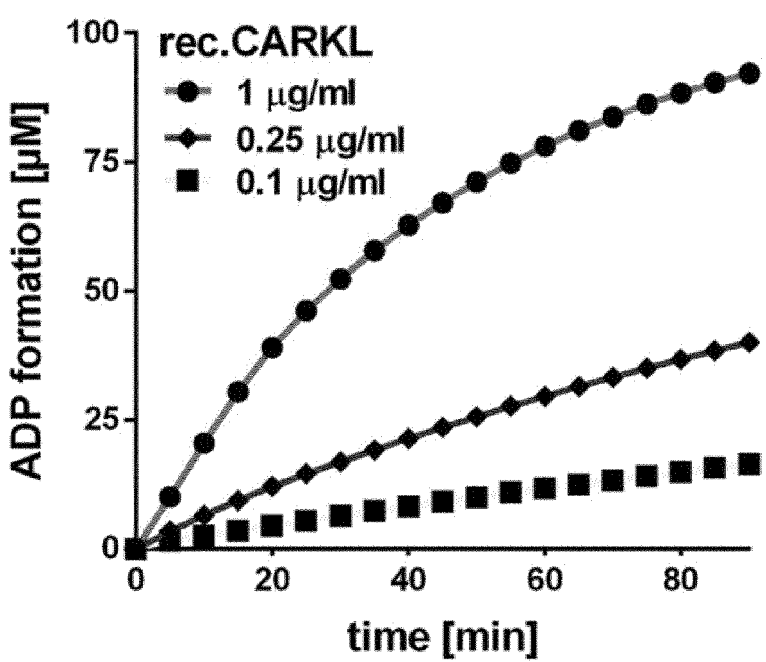
Figure 4:
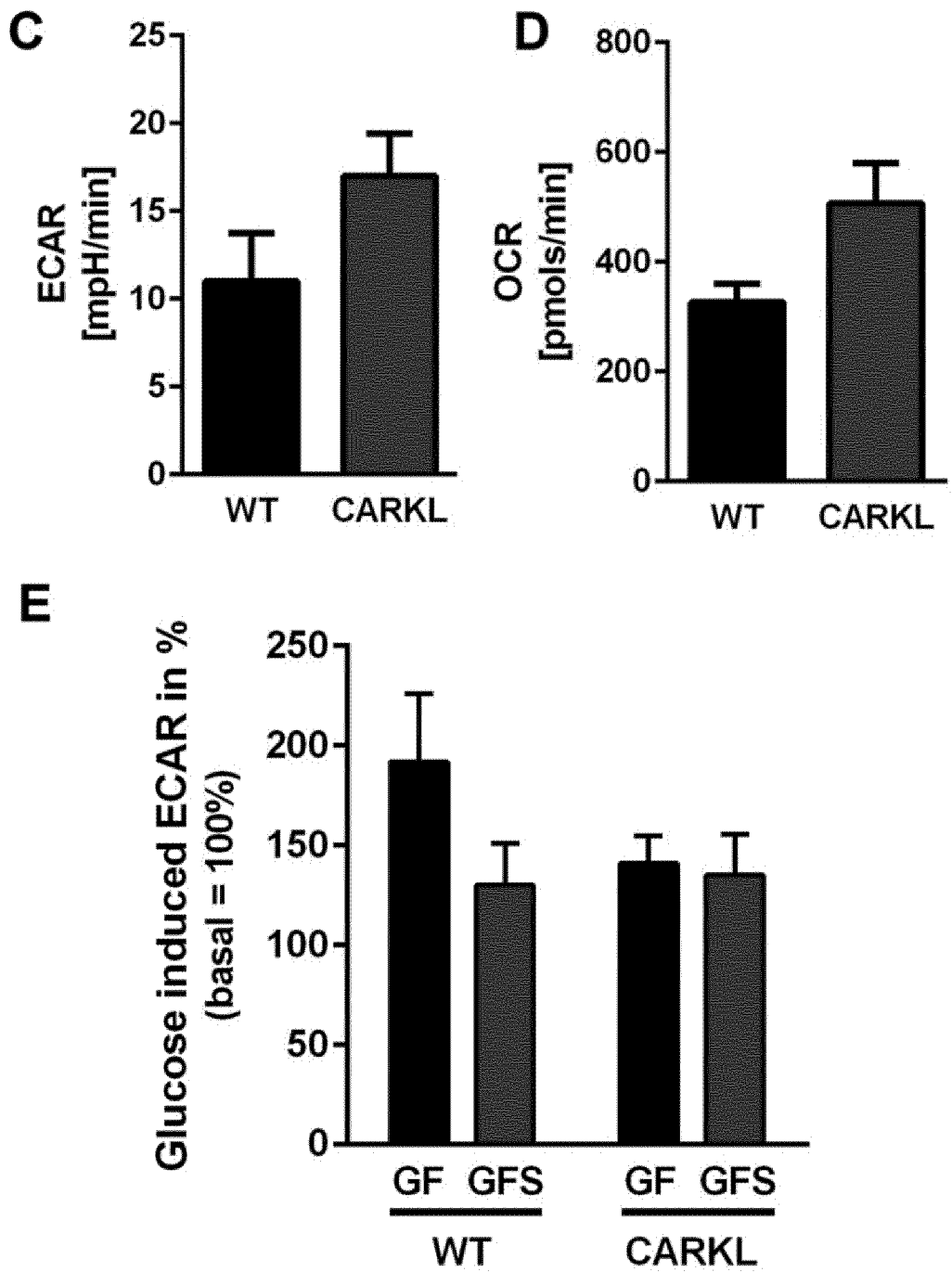
Figure 4:
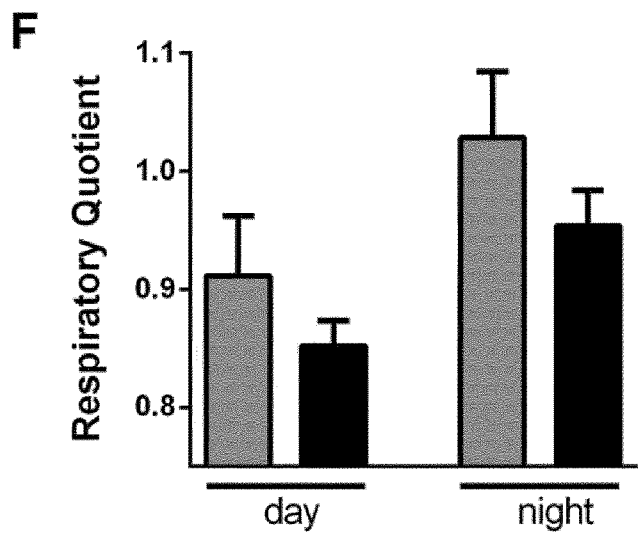
Figure 4:
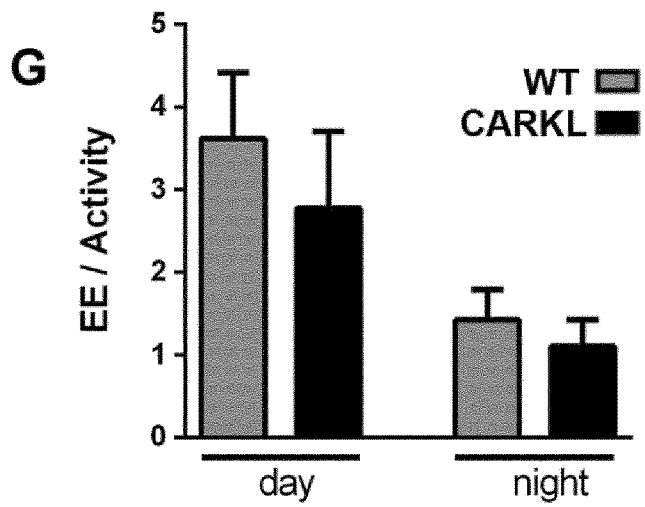
Figure 4:
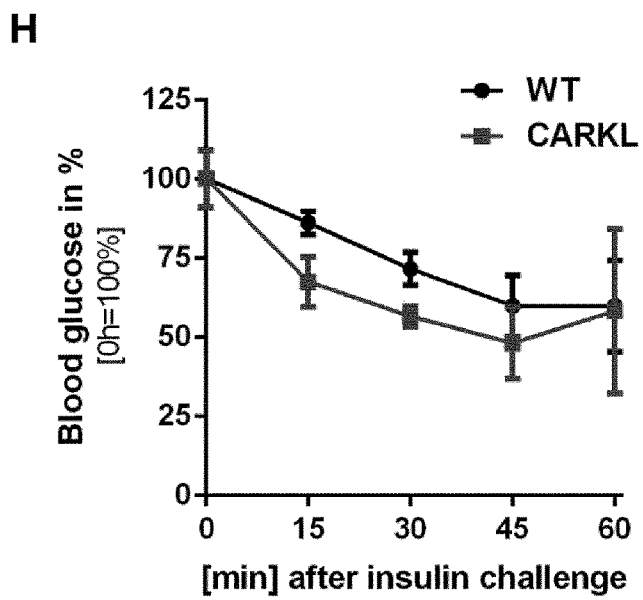

FIG. 4: In an in vitro kinase assay, which employs ADP formation as activity readout, the sedoheptulose turnover rate at constant ATP (150 μM) concentration was enhanced either by (A) increasing sedoheptulose concentration or (B) by increasing the amount of the rate-limiting enzyme sedoheptulose kinase (CARKL). (C-E) Hepatocytes from wilt-type (WT) and sedoheptulose kinase CARKL overexpressing mice were pre-cultured for two days in GFS containing media before basal (C) ECAR and (D) OCR was recorded of these cells. (E) Hepatocytes from both genetic linages (CARKL and WT controls) were cultivated in GF or GFS containing media and then pre-starved (no-carbohydrates) for 1 h to measure glucose-induced ECAR after the addition of glucose to reach a final concentration of 1 g/L in the culture media mean+/−S.D., n=7-11). As metabolic in vivo indicators (F) the respiratory quotient (RQ) and (G) energy expenditure (EE, kcal/day/kg^0.75) per activity by indirect calorimetry were determined and compared CARKL to wild-type (WT) littermates during day (8 am to 4 pm) and night (8 pm to 4 am). Data represent mean values, n=3, +/−SD. (H) Insulin tolerance test in mice was performed on pre-starved (4 h) female CARKL-transgenic and wild type littermate controls by i.p. injection of 0.75 U insulin/kg body weight. Blood glucose was measured before the injection (control) and 15, 30, 45 and 60 minutes after injection and graphed as relative value in % of control. Data represent mean values+/−SD, n=3-4.

Figure 5:
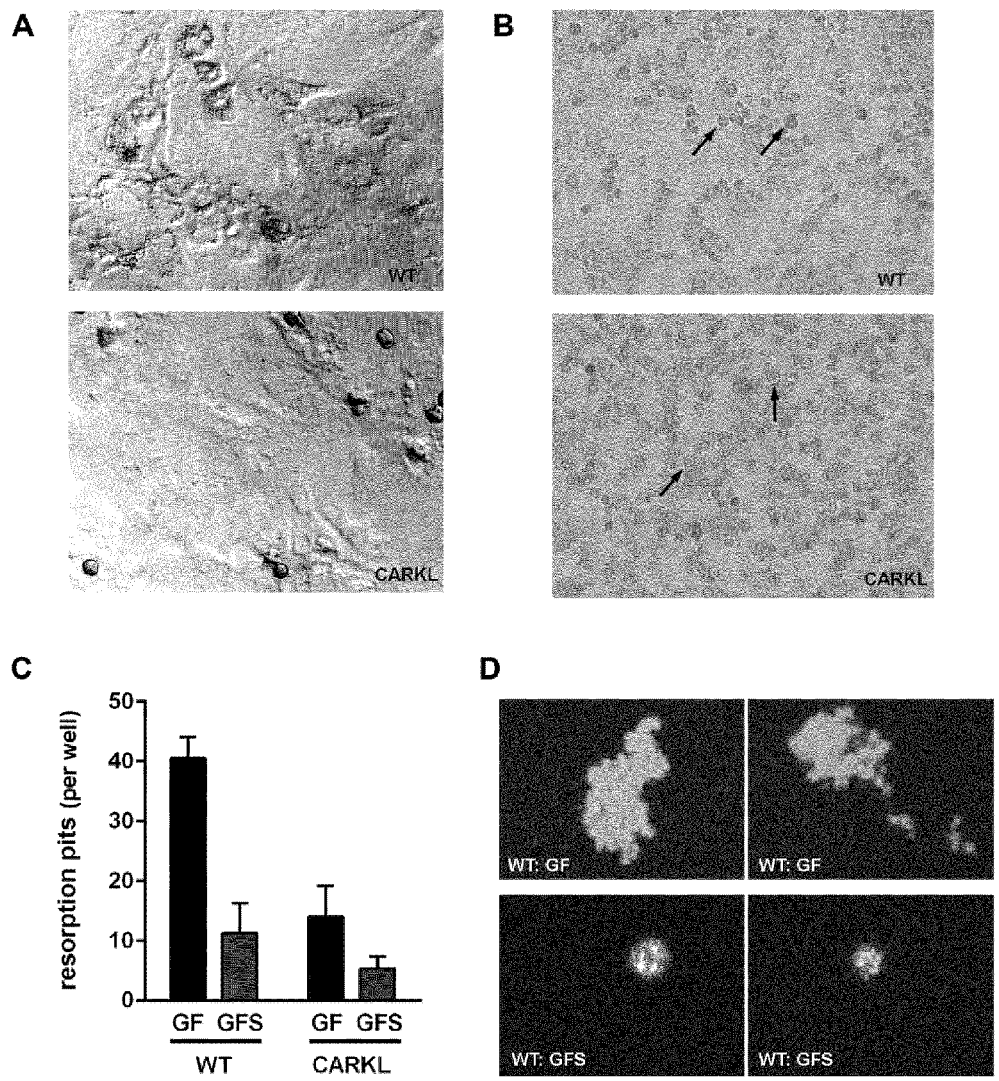

FIG. 5: (A) Lipid deposition in hepatocytes isolated from either WT or CARKL overexpressing mice and cultivated in control medium (GF) was visualized by oil red staining. Representative micrographs were acquired with a 20× objective. (B) Glucose-6-phosphate dehydrogenase activity was measured in hepatocytes isolated from either WT or CARKL overexpressing mice and cultivated in control medium (GF) for two days. Arrows indicate re-localization of G6PD activity. Representative micrographs were acquired with a 10× objective. (C and D) Osteoclasts from WT or CARKL overexpressing mice were differentiated and cultivated for 7 days in Corning Osteo Assay plates in GF or GFS containing media. Their resorption-activity was assessed by counting all pits per well which were visible at 20× magnification. Data represent mean values, n=2-3, +/−SD. (D) Two representative images of the largest resorption-pits found in WT osteoclast either cultured in GF or GFS containing media are shown. Micrographs were acquired by 40× magnification.

Figure 6:
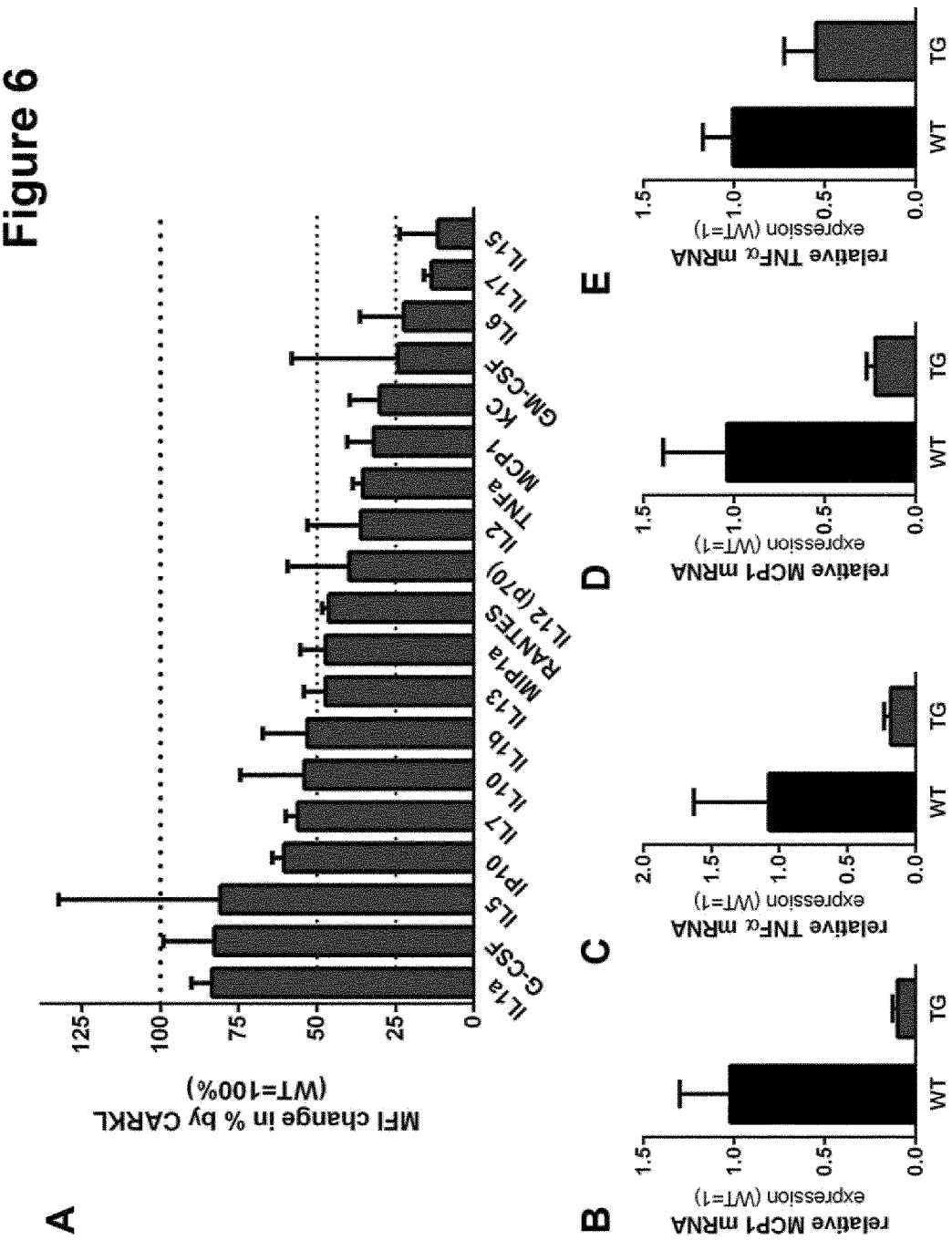
Figure 6:
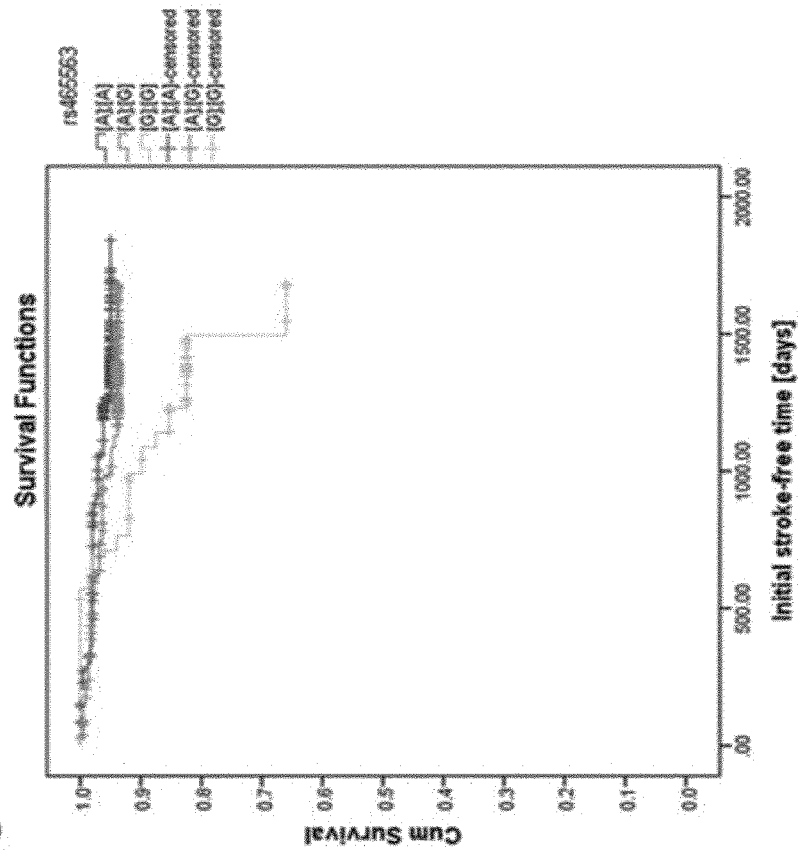
Figure 6:
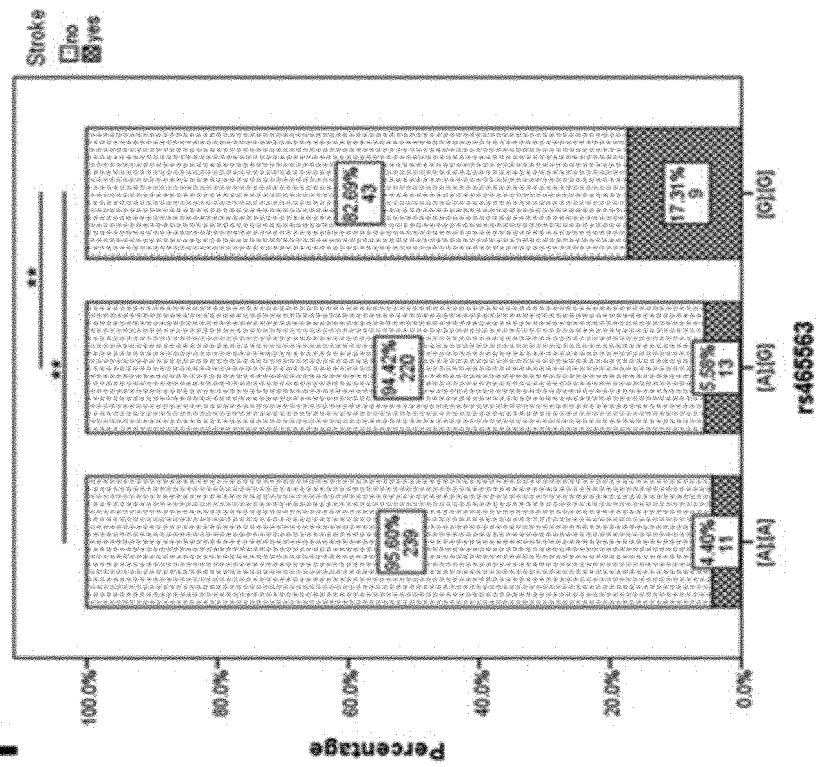

FIG. 6: (A) The immune system of sedoheptulose kinase overexpressing mice (CARKL) and control littermates was challenged with a sub-lethal lipopolysaccharide injection (LPS, 7 mg/kg) and a panel of 19 cytokines was measured 24 hrs after immune activation in serum. Data represents relative mean fluorescence intensities (MFI) of individual cytokines measured in wild type (WT=100%) and CARKL serum by milliplex map mouse cytokine profiler (n=3, +/−SD). Monocyte chemoattractant protein-1 (MCP-1) and TNFa mRNA expression of murine mature adipocytes isolated from (B and C) subcutaneous or (D and E) epididymal white adipose tissue of WT and CARKL mice. Data represent mean values, n=3, +/−SD. (F) Incidence of stroke and rs465563 genotype. Data were compared by Pearson's $\chi^2$-tests. ** . . . p<0.01. (G) Duration of initial stroke-free survival was assessed by Kaplan-Meier plots. Individuals homozygous for the rs465563: [G]-allele show significantly shorter event-free times than carriers of the [A]-allele.

EXAMPLES

Materials and Methods

Carbohydrates

Glucose and fructose were purchased from Sigma Aldrich. Sedoheptulose was isolated from the plant sedum Spectabile or sedum telephium (Haschemi et al., Cell Metab. 15 (2012), 813-826) and was further purified by chromatography.

Glucose and Sedoheptulose Measurements in Carrots and Human Serum

Fresh carrots with an Austrian "organic-certificate" were sliced into small pieces and snap-frozen in liquid nitrogen. The same procedure was applied to leaves freshly harvested from indoor-grown Sedum Spectabile plants. Three samples of each tissue were pooled and homogenized to powder by glass-beads. The carbohydrate rich fractions of the samples were isolated by 20% $H_2O$ and 80% MeOH extraction solution spiked with 13C standards and processed for standard gas-chromatography coupled to mass spectrometry (GC-MS). Glucose and sedoheptulose were identified by their individual masses and their relative amount was derived from the peak area of each individual analyte normalized to 13C content. Glucose and sedoheptulose were also measured in equal volumes of serum from overnight fasted or carrot fed individuals. The carrots were steamed and some olive-oil, salt and pepper were used for flavour. Two hours before and two hours after the carrot containing meal human serum was prepared in VACUETTE® Z Serum Sep tubes from blood. Serum samples were processed as previously described and also analyzed by GC-MS as detailed above and in Ruiz-Matute A I et al., Chromatogr B Analyt Technol Biomed Life Sci. (2011) May 15 879(17-18).

Glucose, Fructose and Sedoheptulose Concentration in Beverages

Indicated beverages were purchased from a local grocery store and were all pre-packed. From each beverage 1 ml (for each of four technical replicates) was aliquoted and vacuum concentrated on a SpeedVac. This was followed by MeOH/H2O (80:20) precipitation and a centrifugation step to clear the carbohydrate fraction in the supernatant from precipitate. Each supernatant was again lyophilized in a SpeedVac, rehydrated in equal volumes of water and technical replicates were pooled. For carbohydrate analysis a Dionex ICS-3000 DC metal-free system was used with a CarboPac PA1 column (250×4 mm) and a CarboPac PA1 guard column (both from Dionex) at a flow rate of 1 mL min-1. Elution was carried out isocratically with 16 mM NaOH for the first 20 min. Then a linear gradient to 100 mM NaOH was applied from 20 to 40 min followed by an increase over two minutes to 200 mM hold until 47 min. The starting condition with 16 mM NaOH was reached again at 49 min and kept until 70 min. Parameters of the pulsed amperometric detection are exactly as recommended in the Technical Note 21 (Optimal Settings for Pulsed Amperometric Detection of Carbohydrates Using the Dionex ED40 Electrochemical Detector) from Dionex. Chromatograms were evaluated according to chromatograms of authentic glucose, fructose and sedoheptulose standards, each 100 µM.

Human Adipocyte Culture

Stromal vascular fraction cells (SVFs) from subcutaneous white adipose tissue of a patient undergoing abdominal surgery were isolated as described before (Lindroos et al, Cell Metab. (2013), Jul. 2; 18(1):62-74.). Briefly, adipose tissue was digested with Collagenase II (Worthington) and filtered. SVFs were separated from mature adipocytes by centrifugation, followed by the lysis of erythrocytes in the SVF-fraction (Buffer EL, Qiagen). The purified SVFs were cultured in DMEM/F12, 10% FBS (Gibco, Life Technologies). As soon as the cells reached confluence, they were washed with DMEM/F12 w/o glucose (Biowest) and the medium was replaced by DMEM/F12 with a total carbohydrate load of 3 g/L, containing 1.5 g/L glucose and fructose or 1 g/L each of glucose, fructose, and sedoheptulose, respectively. Two days after confluence (day 0), differentiation was induced by adding 1 µM dexamethasone, 1.74 µM insulin, 5 µM troglitazone, 0.5 µM IBMX, 17 µM pantothenic acid and 33 µM biotin. After two days, IBMX and dexamethasone were omitted, while insulin and troglitazone were removed on day 4. 50% of the medium was replaced on day 6. Two days later, the cells were harvested for RNA isolation (RNeasy mini kit, Qiagen).

Mature Murine Adipocytes Ceiling Culture

Anterior and posterior subcutaneous adipose tissue and epididymal white adipose tissue was isolated from transgenic CARKL-mice and wild-type littermate controls. Adipose tissue was digested as described above for the human sample. After centrifugation, the layer of floating mature adipocytes was removed and re-centrifuged at 100 rcf for 10 minutes. 150 µL of packed adipocytes were cultured under a floating coverslip in six-well plates, in DMEM/F12, 15% calf serum (PAA). 24 hours after isolation, the wells were washed twice with PBS and the medium was exchanged to DMEM/F12 with a total carbohydrate load of 3 g/L, containing 1.5 g/L glucose and fructose, or 1 g/L each of glucose, fructose and sedoheptulose, respectively. Three days later, the cells were harvested for RNA isolation using TRIreagent (Sigma).

Hepatocyte Culture

Hepatocytes were isolated from male wild-type and CARKL overexpressing mice after the mice were sacrificed by hepatic in situ collagenase perfusion. After perfusion, the liver was quickly removed, minced, and filtered through a cell strainer (Fisher Scientific, Inc) into a 50 ml sterile tube. Hepatocytes in the resulting filtrate were purified from the nonparenchymal cells by centrifugation steps. The isolated hepatocytes were seeded into plates at a concentration of $0.25 \times 10^6$/ml in respective DMEM-media containing 10% FBS and indicated carbohydrate mixes at 3 g/L (glucose and fructose (GF), or glucose, fructose and sedoheptulose (GFS)) at least two days before experiments were performed.

Bone Marrow Derived Macrophages and Osteoclasts Culture

Mouse bones were isolated from male wild-type and CARKL overexpressing mice and bone marrow wash flushed, washed and cleared from redblood cells by lysis, and subsequently differentiated in DMEM containing 25 mM glucose and 20 ng/ml M-CSF. After 4 days, cells for osteoclast differentiation were harvested and seeded in corning osteo assay plates with differentiation media (see below), and for primary bone marrow derived macrophages (BMDM) the medium was renewed and further supplemented with M-SCF for two days. Differentiated BMDM were then seeded in respective DMEM-media containing 10% FBS and indicated carbohydrate mixes at 3 g/L (glucose and fructose (GF), or glucose, fructose and sedoheptulose (GFS)) at least two days before experiments were performed.

In Vitro Bone Resorption Assay

Osteoclast precursor cells (bone marrow cells treated with 20 ng/ml M-CSF for 4 days) were plated in 24-well Corning Osteo Assay plate in the presence of 10 ng/ml M-CSF and 100 ng/ml RANKL in alpha-MEM medium containing 10% FBS and 3 g/L either glucose and fructose (GF), or glucose, fructose, and sedoheptulose (GFS). The Medium was renewed every third day. After 7 days, cells were removed with bleach and washed three times with water before Von Kossa staining according to standard protocols from Corning (technical review) was performed to enhance contrast between the intact assay surface and resorption pit. Each well was entirely photographed by TissueFax with an ×20 objective and all visible resorption pits were counted and analysed blinded.

Extracellular Acidification Rates and Oxygen Consumption Rates

The XF-Analyzer (Seahorse Bio.) was used to measure changes in cellular metabolism induced by different carbohydrates. Extracellular acidification rates (ECAR, mpH/min) and oxygen consumption rates (OCR, pmoles/min) were recorded in primary human adipocytes and primary murine hepatocytes according to the manufacture instructions. Briefly, cells were seeded in seahorse cell plates at a density of 10^4 cells per well for adipocytes and 0.5×10^5 cells per well for hepatocytes. At the day of experiments the cells were washed with carbohydrate free media and incubated for one hour in indicated media containing carbohydrate mixes at a concentration of 3 g/L (glucose and fructose (GF), or glucose, fructose and sedoheptulose (GFS)). To measure glucose-induced ECAR, cells were starved for one hour in carbon free media before glucose (1 g/L) was added to the well per automatic injection. Glucose-induced ECAR was normalized to respective ECAR before glucose addition (basal=100%). Changes induced by the different carbohydrate sources were expressed as relative change in % to illustrate the effect of each carbon source.

Gene Expression Analysis

Briefly, total RNA was extracted and reverse-transcribed using commercial kits (QIAGEN, Applied Biosystems). Quantitative real-time PCRs were performed on an Abi-PRISM 7900HT real-time cycler using iTaq SYBR Green Supermix with ROX (BioRad) to measure CARKL, adiponectin, UCP-1, TNFa, IL-6, MCP-1, and beta-actin expression as previously described (Haschemi et al., Cell Metab. 15 (2012), 813-826). Expression of target gene was normalized to beta-actin expression. Relative expression of target gene was calculated by the delta-delta CT method.

Sedoheptulose Kinase Assay

The ADP Quest Assay (DiscoveRx) was used to indirectly measure S7P formation by ADP accumulation over time according to the manufacture instructions. Recombinant sedoheptulose kinase was previously produced in $E.$ $coli$ and purified by affinity purification (Haschemi et al., Cell Metab. 15 (2012), 813-826).

Indirect Calorimetry

The respiratory quotient (VCO2 production/VO2 consumption) and energy expenditure (EE, kcal/day/kg^0.75) per activity of mice were measured in metabolic cages (Harvard Apperatus) by indirect calorimetry. Either one CARKL transgenic mouse or a wild-type littermate, was housed per cage for one day before it was started to record mean respiratory quotient and energy expenditure per activity during day (8 am to 4 pm) and night (8 pm to 4 am).

Insulin Tolerance Test

Four hours pre-starved female CARKL-transgenic mice and wild type littermate controls were i.p. injected with 0.75 U insulin/kg body weight. Blood glucose was measured before the injection and 15, 30, 45 and 60 minutes after injection by using one-touch glucose strips (Accu Check, Roche).

Oil Red Staining

Briefly, hepatocytes were cultured as indicated before the medium was removed and cells were fixed by 10% formalin. After a wash with 60% isopropanol the wells were incubated with Oil Red O solution (Sigma-Aldrich) and stained for 10 min, washed 4 times with water before photographs were taken at ×20 magnification.

Glucose-6-Phosphate Dehydrogenase Activity Assay

Cells were grown on polystyrene vessel tissue culture treated glass slides, snap frozen in liquid nitrogen and kept at −80° C. The enzyme histochemical procedure was based on the tetrazolium salt method as described by Van Noorden and Frederiks. The incubation medium for the demonstration of G6PD activity contained 18% (w/v) polyvinyl alcohol (average molecular weight 70,000-100,000) in 0.1 M Tris-Maleate buffer, pH 7.5, 15 mM glucose-6-phosphate, 0.8 mM NADP, 0.4 mM magnesium chloride, 0.45 mM 1-methoxyphenazine methosulphate, 5 mM sodium azide and 5 mM tetranitroblue tetrazolium chloride. The medium was freshly prepared immediately before incubation. Control reactions additionally contained 40 mM glucosamine-6-phosphate. Cells were incubated at room temperature for 15 minutes under continuous mixing by orbital shaker. After incubation, cells were washed 3×5 minutes in 60° C. phosphate buffered saline, dried, and mounted in glycerol gelatin, and photographed within one day at ×10 magnification.

Immune Challenge and Cytokine Response Profiling In Vivo

For sublethal murine in vivo endotoxemia, 7 mg/kg LPS (Sigma Aldrich) were injected intraperitoneally in male CARKL transgenic or wild-type littermates. Serum was isolated by VACUETTE® mini Z Serum Sep tubes from whole blood. Cytokine were measured by milliplex map mouse cytokine profiler according to manufactures instructions (Millipore). All animal experiments were carried out according to an ethical animal license protocol and contract approved by the Medical University Vienna (BMWF-66.009/0140-II/10b/2010).

CARKL Single Nucleotide Polymorphism (SNP) Association-Study with Risk of Stroke.

Study Design: 578 neurologically asymptomatic patients from the Inflammation and Carotid Artery—Risk for Atherosclerosis Study (ICARAS, Schillinger et al., (2005) Circulation 111 (17):2203-2209.)), recruited until March 2003, were included into the present analysis—inclusion and exclusion criteria have been published previously. Briefly, asymptomatic carotid artery disease, representing the primary inclusion criterion, was defined as the absence of transient ischemic attacks (TIA), amaurosis fugax and stroke within the last 12 months or of residual symptoms, respectively. Besides exhaustive medical examination (including anamnesis, physical status and blood testing), patients underwent sonography of the carotid arteries at baseline and at a follow-up 6-9 months after study inclusion as previously described (Schillinger et al., (2005) Circulation 111 (17): 2203-2209.). Incidence of cardiovascular events was recorded until January 2006. This analysis was approved by the local ethics committee (EC-No. 1933/2012) and has been performed in accordance with the ethical standards specified by the Declaration of Helsinki and its amendments.

Definitions: Arterial hypertension was defined as repetitive resting blood pressure above 140/90 mm Hg and was assumed to be present in patients with antihypertensive medication. Hyperlipidemia was diagnosed in patients with a total serum cholesterol >200 mg/dL or LDL cholesterol >130 mg/dL and was considered to be present in all patients taking lipid-lowering drugs. Diabetes mellitus was diagnosed as supposed by Expert Committee on the Diagnosis and Classification of Diabetes Mellitus. Peripheral artery disease was graded using Fontaine's classification system, coronary artery disease was defined according to the classification by the Canadian Cardiovascular Society (CCS).

Anamnestic myocardial infarction was defined according to Alpert. Stroke was defined by a neurological deficit persisting >24 h and was evaluated according to the modified Rankin stroke scale. Progression of carotid artery atherosclerosis was defined as an increase in stenosis by at least one NASCET angiographic degree.

Genotyping: DNA was isolated from EDTA-anticoagulated whole blood by means of spin-column based nucleic acid purification. Genotyping was done on an ABI TaqMan® 7900HT fast-realtime thermocycler (Applied Biosystems, Rotkreuz, Switzerland) using the 5'-Nuclease-Assay [7]. This assay includes the sequence-specific binding of labeled DNA-probes. During the annealing phase of each step, sequence-specific probes containing a fluorophore on their 5'-ends bind their respective allele. The fluorescence of the fluorophore is masked by a 3'-quencher, until the 5'-Taq-polymerase separates these compounds by its 5'-exonuclease activity during the elongation phase. End-point-measurement of the intensity of sequence-specific fluorescence indicates the presence of the corresponding allele. In the present study, rs465563 was analyzed in a total reaction volume of 10 µL using a commercially available TaqMan® SNP genotyping assay (Assay ID: C_717358_1_, Applied Biosystems) and TaqMan® Genotyping Master Mix (Applied Biosystems) according to the standard protocol supplied by the manufacturer. The results were interpreted using SDS 2.4 sequence detection software (Applied Biosystems).

Statistical Analysis: Continuous data are given with respect to its distribution as mean and standard deviation or median and interquartile range. Categorical data are presented as counts and percentage. Presence of normal distribution within subgroups was assessed by Kolmogorov-Smirnov-tests. Metric variables were compared by Mann-Whitney U tests. Connections between genotypes and study end points as well as relative risks were estimated by contingency-tables and Pearson's $\chi^2$-tests. Event-free survival was estimated by Kaplan-Meier-Analysis, data was compared pairwise by Log Rank (Mantel-Cox) tests. Multivariable models were calculated by means of binary logistic regression and evaluated by drawing ROC (Receiver-Operator-Characteristics) plots. Results were considered statistically significant at $p<0.05$ unless otherwise noted. All p-values were interpreted two-sided unless otherwise stated. All statistical calculations were done using IBM SPSS 20.0 (IBM Corporation, Armonk, USA).

Results

Diet-Derived Sedoheptulose Uptake in Humans

To determine if nutritional sedoheptulose is absorbed from diets via the digestive tract into the human blood, which is a critical step for sedoheptulose to become a metabolic active carbohydrate, glucose (C6) and sedoheptulose (C7) levels were measured in carrots and in human serum. To determine the C6/C7 ratio of carrots plant tissue was homogenized, extracted the small molecule fractions and measured simultaneously relative glucose and sedoheptulose amounts by GC-MS (FIG. 1A). Leaves of Sedum Spectabile, a succulent plant which contains high sedoheptulose levels, were analyzed in parallel as positive control. The leaves of Sedum Spectabile contained glucose and approximately twice as much sedoheptulose, which resulted in a C6/C7 ratio of approximately 0.5. In fresh food grade organic carrots almost equal quantities of glucose and sedoheptulose were detected and thereby a C6/C7 ratio of around 1. Potatoes, in contrast to carrots, were reported to contain no sedoheptulose (Kardon et al., FEBS Lett. (2008) Oct. 15, 582(23-24)) and are therefore expected to possess a very high (or even infinite) C6/C7 ratio. Next it was addressed if diet-derived sedoheptulose, originating from carrots, reaches the human blood by monitoring serum level of glucose and sedoheptulose before and after a meal containing mainly steamed carrots (~700 g per male adult) with some olive-oil, salt and pepper. Two hours after the meal, an approximately two-fold increase in sedoheptulose serum levels was observed in humans (FIG. 1B). This result clearly indicated that nutritional sedoheptulose is absorbed by the human digestive tract and that it enters the blood to become available as a carbohydrate for subsequent metabolism. Serum glucose levels normalized already within two hours after food uptake and thereby suggest that humans metabolize sedoheptulose and glucose differently.

These results indicate that carrots, which are considered as healthy vegetables and constituents of diets around the world, are a natural sedoheptulose source for humans. It is interesting to mention that carrots, although they contain carbohydrates such as glucose, are suitable and well tolerated by diabetics and even protect people with common genetic risk factors for type-2 diabetes (Patel C J et al., Hum Genet. 132 (2013): 495-508).

The C6/C7 Ratio in Natural and Manufactured Human Food Products

Next, the concentration of glucose, fructose and sedoheptulose was measured in carbohydrate extracts from Coca-Cola®, Red Bull®, orange-, apple-, tomato-, and carrot-juice to establish the C6/C7 index for common beverages and thereby estimate the actual human sedoheptulose-exposure. Soft- and energy drinks contained glucose and fructose but no sedoheptulose (FIG. 1C). Fruit-juices contained similar amounts of C6 (the sum of glucose and fructose) as soft-/energy drinks (100 mM range), but in contrast to the latter they also contained sedoheptulose in the 100 µM range. In vegetable-juices glucose and fructose levels were reduced, whereas sedoheptulose concentrations were found greatly increased (mM range). The C6/C7 ratios of the individual beverages, calculated as molar—as well as weight ratios, are given in FIG. 1D. In two fruit-juices C6/C7 ratios of around 2000/1 were found. In tomato- and carrot-juices the ratio was 75/1 and 20/1, respectively; Coca-Cola® and Red Bull® contained no detectable amounts of sedoheptulose. Hence, the C6/C7 ratio for these drinks could not be calculated and is therefore not applicable (N.A.) to such food products if they are not additionally supplemented with C7. These findings clearly indicate that manufactured food products lack carbohydrate complexity and therefore also sedoheptulose. Notably, in absolute numbers these data indicate that 1 kg of diet-derived sedoheptulose is consumed per 9 kg diet-derived glucose if the natural carbon-mixture of carrot-juice was chosen over soft-/energy drinks—the consequences of chronic sedoheptulose deprivation by an unbalanced human nutrition are currently unknown.

Sedoheptulose Kinase Oscillates and is Highly Expressed in Metabolically Active Tissue.

To understand how sedoheptulose kinase CARKL and therefore sedoheptulose metabolism is distributed and controlled in various mammalian tissues, different tissues were tested for mRNA expression levels. CARKL expression, in a publicly available database for circadian expression profiles (CircaDB), was found oscillating in mouse liver (period 20.0, FIG. 2A) and adrenal gland (period 24.0, data not shown). Sedoheptulose-7P levels were previously reported to oscillate in plants, peaking during the regenerative-phase of carbon-fixation to reconvert ribose moieties. The mammalian circadian clock is in part set by the redox-state. CARKL overexpressing RAW264.7 cells indicated that high sedoheptulose kinase expression induces a 4 fold increase of redox-factors like reduced nicotinamide, adenine dinucleotide (NADH) and also glutathione (GSH) level increase (FIG. 2B and Haschemi et al., Cell Metab. 15 (2012), 813-826). Deficiency of CARKL and therefore also lack of sedoheptulose turnover showed the opposite effect (FIG. 2C). This data indicates that sedoheptulose metabolism is under the control of circadian rhythm and acts simultaneously as modulator of cellular redox-states. In order to specify which tissue consumes nutritional sedoheptulose, mRNA levels of sedoheptulose kinase (CARKL) were measured in a mouse cDNA tissue library (FIG. 2D). Sedoheptulose kinase is the rate-limiting enzyme of sedoheptulose metabolism and was highly expressed in liver, kidney, in brown and white adipose tissue (BAT and WAT), digestive organs, in glands, in the male reproductive system as well as in the brain. These results demonstrate that diet-derived sedoheptulose can become a systemic carbohydrate source for many tissues but especially for metabolically active organs such as the liver, kidney and adipose tissue.

Sedoheptulose Metabolism is Important for the Function and Metabolic Health of Cells To investigate the metabolic consequences of exposure to sedoheptulose, human and murine cells in the culture media were exposed to either glucose in combination with fructose (GF) or to glucose, fructose and sedoheptulose (GFS), while keeping the total carbohydrate load constant. The function of adipocytes, hepatocytes and macrophages was tested to evaluate the importance of sedoheptulose in complementing nutritional carbohydrate loads. The sedoheptulose used in these experiments was isolated from *sedum telephium* plants.

In the human body, adipocytes fulfil the crucial function to store energy in form of lipids and are therefore very important cells to maintain health. In metabolically unhealthy or in most morbidly obese patients adipocytes do not function properly, increase their cell size to account for excessive lipid loads, become inflamed (meta-inflammation, a low-grade but chronic type of inflammation) and ultimately contribute to the development of disorders like insulin resistance or cardio-vascular diseases. In human adipocytes, differentiated from subcutaneous precursor cells, an increase in sedoheptulose kinase CARKL mRNA expression was found if sedoheptulose was added to the culture media (FIG. 3A). Furthermore, an increase in adiponectin and UCP-1 expression, two functional relevant adipocyte marker genes, was observed in the GFS compared to GF treated cells (FIGS. 3B and 3C). To test for changes in cellular metabolism, cellular oxygen consumption rates (OCR) and extracellular acidification rates (ECAR) were measured as indicators for mitochondrial respiration and lactic acid fermentation, respectively. Human adipocytes, differentiated and cultured in sedoheptulose containing media, showed comparable ECAR to WT controls, while their cellular oxygen consumption rates were increased (FIGS. 3D and 3E).

Together, these data show that subcutaneous adipocytes maintain and improve their function (increase in adiponectin, UCP-1 and oxygen consumption) in the presence of sedoheptulose compared to a situation where only glucose and fructose are present as bio-fuel.

To better define the beneficial role of sedoheptulose in preventing metabolically unhealthy states like chronic low-grade inflammation, the cytokine profiles of primary mature murine adipocytes, primary murine hepatocytes, and naïve as well as lipopolysaccharide (LPS)-induced activated primary macrophages cultured in GF or GFS media were measured. Mature adipocytes, which were cultivated in sedoheptulose containing media, produced less TNFa and IL-6 mRNA than adipocytes cultivated with glucose and fructose alone (FIGS. 3F and 3G). Similarly to that, hepatocytes also produced less IL-6 if cultivated with sedoheptulose (FIG. 3H). In primary macrophages basal TNFa and IL-6 mRNA expression, and cytokine secretion were found blocked by sedoheptulose containing media (FIG. 3I-L). LPS-induced macrophage activation resulted in strongly enhanced TNF-a and IL-6 secretion in GF cultured cells (FIGS. 3M and 3N). LPS-induced macrophages cultivated in GFS media increased IL-6 to comparable levels as GF treated macrophages, but reduced their TNFa secretion by approximately 40%. This shows that addition of sedoheptulose to macrophages on the one hand reduces their basal inflammatory state, measured by TNFa and IL-6, but on the other hand retains their natural function in immunity as seen for IL-6.

To conclude, addition of sedoheptulose to the culture media significantly enhanced subcutaneous adipocyte function and reduced the inflammatory state of cells and thereby might positively influence the pathogenesis of obesity, type II diabetes and cardiovascular diseases also summarized in part by the metabolic syndrome.

Sedoheptulose Kinase CARKL Overexpression

Transgenic mice overexpressing sedoheptulose kinase ubiquitously in the entire body were generated to isolate genetically engineered primary cells overexpressing CARKL and to test sedoheptulose metabolism in vivo. CARKL transgenic mice did not show any obvious phenotypes and their organ weight was not different to organ weights of WT littermate control animals (data not shown). It was hypothesized that increased sedoheptulose metabolism can either be achieved by increasing the concentration of the substrate sedoheptulose, or by elevating the level of its rate-limiting enzyme sedoheptulose kinase (CARKL). To test this in an in vitro kinase assay, a constant amount of recombinant CARKL protein was incubated with increased doses of sedoheptulose. This resulted in enhanced sedoheptulose turnover rates as measured by ADP formation (FIG. 4A). The same effect was observed by increasing CARKL protein concentration, while sedoheptulose concentration was kept constant (FIG. 4B). These results demonstrate that CARKL overexpression is a valid model to investigate the effects of increased sedoheptulose metabolism. Next, primary hepatocytes, as liver tissue appeared to endogenously metabolize sedoheptulose (FIG. 2D), were isolated to study the effects of C7- and C6-metabolism at increased CARKL expression levels.

Hepatocytes were cultured in media with a C6/C7 sugar ratio of 2:1 and metabolically assessed by comparing the ECAR and OCR as more general metabolic-parameters. Hepatocytes from CARKL overexpressing mice significantly increased their metabolic rate as increased ECAR and OCR levels indicated if compared to WT control cells (FIGS. 4C and 4D). It appeared that sedoheptulose induced a more efficient metabolism in these cells. To test for the relevance of sedoheptulose and sedoheptulose kinase expression together, hepatocytes isolated from WT and CARKL mice were incubated in GF and GFS containing culture media and their glucose-induced ECAR was compared (after 1 hr carbohydrate starvation) as a measure to control cellular glycolysis. In WT hepatocytes glucose-induced ECAR was reduced by sedoheptulose administration (FIG. 4E). In line with this data, glucose-stimulated hepatocytes from WT animals cultured in GF (without sedoheptulose) routed a larger part of glucose to lactic acid fermentation, whereas cells from CARKL overexpressing mice appeared to balance the same glucose bolus more efficiently.

These results further supported the previous data and clearly pointed out that increased sedoheptulose metabolism has distinct and beneficial effects on cells, which are important for metabolic health.

Sedoheptulose Metabolism In Vivo

After validating cellular phenotypes of sedoheptulose kinase overexpression in hepatocytes the metabolic effect of increased sedoheptulose turnover to an entire organism was investigated by comparing the respiratory quotient (RQ; RQ=exhaled $CO_2$/oxygen consumption), as well as energy expenditure per physical activity of control and sedoheptulose kinase transgenic mice, measured by indirect calorimetry during day and night as systemic indicators of metabolism (FIGS. 4F and 4G). Sedoheptulose kinase overexpressing animals (CARKL) have lower RQ values compared to wild type (WT) littermates. CARKL mice showed increased oxygen consumption and therefore lower RQ values, and thereby partly mirrored the effects of sedoheptulose on cells. Furthermore, CARKL mice also tend to have a lower EE per activity if compared to control mice. The insulin sensitivity of female CARKL transgenic and WT mice were also compared by an insulin tolerance test (ITT), to investigate if sedoheptulose metabolism also affects insulin signalling in vivo. Insulin injection (i.p.) lowered the blood glucose level in mice overexpressing sedoheptulose kinase faster than in WT controls, indicating that insulin sensitivity was also increased in these animals by increasing sedoheptulose metabolism (FIG. 4H). In this context it is important to mention that induction of insulin resistance in mature adipocytes, by TNFa and hypoxia treatment, resulted in sedoheptulose kinase loss (public Gene expression omnibus data available at http://www.ncbi.nlm.nih.gov/geo/query/acc.cgi?acc=GSM1261655).

Together, these experiments showed that increased sedoheptulose metabolism does not only alter metabolism in vitro but also in vivo. The lower RQ values observed in CARKL mice combined with the by trend lower EE per physical activity and the increased insulin sensitivity are indicative for a more efficient and sustainable metabolic program, which can be induced by increasing sedoheptulose metabolism.

Hepatic Lipid Deposition is Reduced by CARKL

Extensive lipid deposition in hepatocytes results in fatty liver disease and can be accompanied by inflammation (i.e. non-alcoholic steatohepatitis (NASH)) causing liver fibrosis, cirrhosis, and eventually hepatocellular carcinoma. The lipid content of hepatocytes from WT and CARKL overexpressing mice was compared and it was found that hepatocytes from CARKL mice contained less lipid droplets than their WT controls (FIG. 5A).

In conclusion, high liver fat content, especially in combination with inflammation, including malfunction of adipocytes, increases risk of many diseases including type 2 diabetes or cancer, thus both, the reduction of inflammation and lipid accumulation in hepatocytes by sedoheptulose might be especially valuable for human nutrition (see vegetables, which contain high C7 levels).

CARKL Regulates Glucose-6-phosphate Dehydrogenase Activity.

Glucose-6-phosphate dehydrogenase (G6PD), the rate limiting enzyme of the oxidative arm of the pentose phosphate pathway (PPP) which generates C5 bodies i.e. for nucleotide synthesis and redox-equivalents, was previously shown to be directly inhibited by p53 (tumor-suppressor) (Jiang et al., Nat Cell Biol. (2011) March; 13(3):310-6). Mutation in p53, the most frequently mutated gene in human tumors, results in hyper-activation of G6PD and lipid accumulation in hepatocytes. Sedoheptulose kinase is the rate-limiting kinase of the non-oxidative arm of the PPP and was previously shown to reduce the oxidative PPP-flux, at least in macrophages. To test for a possible regulation of G6PD activity in hepatocytes by sedoheptulose metabolism, the enzyme activity of WT and CARKL overexpressing cells was compared (FIG. 5B). In WT control cells G6PD activity was observed to be evenly distributed, whereas in cells from CARKL mice a re-localization of G6PD and thereby a reduced activity in the inner space of the cells was observed. Interestingly, the same phenotype was achieved by incubating WT cells in cell culture media with sedoheptulose (not shown). If re-localization and/or inhibition of G6PD by sedoheptulose kinase overexpression and sedoheptulose incubation were the cause for the reduced lipid accumulation in hepatocytes (FIG. 4A) remains to be established. Nevertheless, this data in combination with data from macrophages shows that an elevated sedoheptulose level may act as a countermeasure for p53 loss in cancer cells, at least by negatively regulating G6PD activity in some instances. Another example are estrogen dependent breast cancer cells which decrease CARKL expression in response to growth factor estrogen (public GeneChip repository data available at http://www.ncbi.nlm.nih.gov/geoprofiles/; ID: 53372898; GDS3285/219713_at/SHPK), which in turn might again result in increased G6PD activity and subsequently tumor growth.

This data also implements sedoheptulose metabolism as a suitable target to regulate G6DP activity and for future anti-cancer strategies.

Sedoheptulose and Bone Metabolism

Bone is an extremely dynamic tissue. The fine balance of bone formation and resorption is essential for the proper mechanical stability of bone. Disequilibrium between bone formation and resorption is the cause of osteoporosis, a highly prevalent condition of reduced bone density and disturbed bone micro-architecture resulting in bone fragility and pathological fractures. As the osteoclasts, the cells responsible for bone resorption are derived from the monocyte lineage, whose function is strongly impacted by sedoheptulose metabolism, it was also tested whether osteoclast function may be modulated by the C6/C7 ratio.

Bone marrow cells were differentiated in vitro to osteoclasts by exposing the cells to M-CSF in combination with RANKL. The cells were cultured in plates, pre-coated with a bone mineral matrix at the bottom of the well, to provide substrate for their bone-resorption activity. Analysis of the substrate resorption clearly demonstrated that both, CARKL overexpression as well as increasing C7 content in the culture media, reduced pit formation by osteoclasts (FIG. 5C). Interestingly, larger resorption-pits were found only in the absence of sedoheptulose (FIG. 5D).

Again, this data supports the concept of the present invention that a well-balanced C6/C7 ratio is crucial to maintain health and that C7 has the potential to alleviate the pathophysiologic situations of i.e. osteoporosis in humans.

Sedoheptulose Kinase Regulates the Immune Response of Animals

Data of CARKL overexpression and its effects on the mouse immune-system in a model of acute immune activation and in low-grade inflammation of mature adipose tissue is presented with the present examples. In CARKL mice acute-inflammation was elicited by a sub-lethal lipopolysaccharide (LPS) injection, which resulted in a suppressed cytokine response compared to wild-type controls (FIG. 6A). A panel of 19 cytokines was measured in WT and CARKL mouse serum, which was isolated 24 hrs after LPS injection (7 mg/kg, IP), by mouse cytokine profiler. Twelve cytokines reached the threshold of 50% mean change, which was defined as cut-off to highlight cytokines regulated by CARKL overexpression in vivo. IL-13, MIP1α, RNATES, IL-12 (p70), IL-2, TNF-α, MCP1, KC, GM-CSF, IL-6, IL-17 and IL-15 were decreased by at least 50% mean change in CARKL mice compared to wild-type littermates. Cytokines IL-6, IL-17 and IL-15 even reached a threshold of 75% mean change. In addition to acute-inflammation, the basal levels of pro-inflammatory cytokines in mature adipose tissue were also assessed from two different depots (subcutaneous and epididymal adipose tissue) of CARKL and WT control mice. Consistently with the reduction in LPS-induced inflammation, mRNA levels of TNFa and MCP1, a primary adipokine which recruits macrophages to adipose tissue and which belongs to the pro-inflammatory cytokines, were found blunted by CARKL overexpression (FIG. 6B-E).

This indicates that a nutritional supplement containing sedoheptulose might dampen acute and low-grade chronic inflammation. Therefore, targeting C7 metabolism, either by nutritional or clinically applied sedoheptulose appears as an effective measure to reduce inflammation and associated disorders.

A single nucleotide polymorphism (SNP) in the 3'-UTR of the CARKL gene is associated with the risk of stroke.

535 neurologically asymptomatic patients from the Inflammation and Carotid Artery—Risk for Atherosclerosis Study (ICARAS, Schillinger et al., (2005) Circulation 111 (17):2203-2209) were genotyped for the rs465563 [A] to [G] substitution in the 3'-UTR of the CARKL gene. 33 (6.2%) patients suffered a stroke within the observation period. In those patients, the distribution of rs465563 alleles was significantly different compared to the allele frequencies of the rest of the study population ($\chi^2$=12.639, df=2, p=0.002, see FIG. 6F). In detail, homozygous carriers of the [G]-allele bore a relative risk of 3.93 (95% CI: 1.72-9.01) compared to [A]-homozygous, and 3.10 (95% CI: 1.40-6.87) compared to heterozygous individuals, respectively. Statistical independence of rs465563 genotype information was assessed by a binary logistic regression model providing age, sex, histories of myocardial infarction and stroke, nicotine consumption, body mass index, as well as certain comorbidities (hyperlipidemia, hypertension, diabetes mellitus) as covariates (model: $\chi^2$=30.476, df=11, p=0.001). Within this model, carrier status of the [G];[G] genotype presented as significant predictor (odds ratio=5.015, 95% CI: 1.803-13.943) when compared to patients homozygous for the [A]-allele. Moreover, it has been assessed by drawing Kaplan-Meier plots whether initial stroke-free survival time depends on rs465563 carrier status. Indeed, homozygous carriers of the [G]-allele (1518.3 days, 95% CI: 1419.2-1617.4) presented with significantly shorter event-free survival than heterozygous individuals (1619.1 days, 95% CI: 1584.8-1653.3, p=0.005) and carriers of the [A];[A]-genotype (1788.1 days, 95% CI: 1755.7-1820.4, p=4.9·10−4) (FIG. 6G). Individuals homozygous for the rs465563: [G]-allele show significantly shorter event-free times than carriers of the [A]-allele.

The mechanistical background of this clinical association remains to be clarified. However, given the ability of CARKL to modulate macrophage polarization and the key role of the latter in the formation and progression of atherosclerotic plaques, it seems likely that the rs465563 polymorphism may impact on the risk of cerebrovascular events via modulation of macrophage polarization within atherosclerotic plaques. This notion is supported by the observation according to the present invention that the 3'-UTR of the CARKL gene is mainly transcribed in macrophages.

In conclusion, this association and the provided data on metabolism and function of adipocytes, hepatocytes, and macrophages in combination with reduced inflammation and enhanced insulin sensitivity in vitro and in vivo strongly indicates that sedoheptulose (C7-sugar) is a critical constituent for human nutrition and simultaneously a highly relevant medication to treat i.e. C7-deficiencies or other metabolic unhealthy disease states.

The invention claimed is:

1. A method of treating inflammation comprising:
   obtaining sedoheptulose; and
   administering said sedoheptulose to a subject;
   wherein inflammation is treated in the subject and the inflammation is further defined as:
   a systemic inflammatory response syndrome (SIRS) or sepsis;
   involved, causally or otherwise, in pathogenesis of adiposity, Crohn's disease, multiple sclerosis, diabetic polyneuropathy, Lyme disease, rheumatoid arthritis, ankylosing spondylitis, autoimmune connective tissue disorders, myositis, psoriasis, or atopic dermatitis;
   involved in pathogenesis of cancer comprising cancer causation, progression, metastasis, resistance to therapy, relapse after therapy, or a cancer manifestation; or
   involved in acute or chronic transplant rejection or in acute or chronic graft-versus-host disease following autologous, syngeneic or allogeneic bone marrow, peripheral blood stem cell (PBSC) or cord blood transplantation.

2. The method of claim 1, wherein the inflammation is a systemic inflammatory response syndrome (SIRS) or sepsis.

3. The method of claim 2, wherein the inflammation is in response to polytrauma, in response to infection, includes organ-specific manifestations, acute respiratory distress syndrome (ARDS) and/or multiple organ dysfunction syndrome (MODS).

4. The method of claim 1, wherein the inflammation is involved, causally or otherwise, in the pathogenesis of adiposity, Crohn's disease, multiple sclerosis, diabetic polyneuropathy, Lyme disease, rheumatoid arthritis, ankylosing spondylitis, autoimmune connective tissue disorders, myositis, psoriasis, or atopic dermatitis.

5. The method of claim 1, wherein the inflammation is involved in the pathogenesis of cancer comprising cancer causation, progression, metastasis, resistance to therapy, relapse after therapy, or a cancer manifestation.

6. The method of claim 5, wherein the cancer manifestation comprises cancer-related cachexia, anemia, fatigue, or depression.

7. The method of claim 1, wherein the inflammation is involved in acute or chronic transplant rejection or in acute or chronic graft-versus-host disease following autologous, syngeneic or allogeneic bone marrow, peripheral blood stem cell (PBSC) or cord blood transplantation.

8. The method of claim 7, wherein the inflammation is involved in acute or chronic transplant rejection of an allogeneic lung, liver, kidney, heart, intestine, or pancreatic islet cell transplant.

9. The method of claim 1, wherein the sedoheptulose is administered in an amount of 0.001 to 300 g per daily dosage.

10. A method for storage of organs for transplantation purposes comprising:

obtaining an organ to be transplanted to a patient; and storing the organ in a storage solution comprising sedoheptulose.

11. The method of claim 10, wherein the storage solution comprises sedoheptulose in a concentration of 0.001 to 500 mg/ml, defined as the concentration of all liquid material attached to or covering the organ to be transplanted.

* * * * *